(12) United States Patent
Ballance et al.

(10) Patent No.: US 8,158,579 B2
(45) Date of Patent: Apr. 17, 2012

(54) FUSION PROTEIN OF AN EXENDIN TO MODIFIED TRANSFERRIN

(75) Inventors: David James Ballance, Berwyn, PA (US); Christopher P. Prior, Rosemont, PA (US); Homayoun Sadeghi, Doylestown, PA (US); Andrew J. Turner, King of Prussia, PA (US)

(73) Assignee: BioRexis Pharmaceutical Corporation, King of Prussia, PA (US)

( * ) Notice: Subject to any disclaimer, the term of this patent is extended or adjusted under 35 U.S.C. 154(b) by 0 days.

(21) Appl. No.: 12/956,623

(22) Filed: Nov. 30, 2010

(65) Prior Publication Data

US 2011/0245178 A1 Oct. 6, 2011

Related U.S. Application Data

(62) Division of application No. 11/782,030, filed on Jul. 24, 2007, now Pat. No. 7,867,972.

(60) Provisional application No. 60/874,965, filed on Dec. 15, 2006, provisional application No. 60/857,474, filed on Nov. 8, 2006, provisional application No. 60/832,582, filed on Jul. 24, 2006.

(51) Int. Cl.
*A61K 38/00* (2006.01)
*A61K 38/26* (2006.01)
*C12P 17/00* (2006.01)

(52) U.S. Cl. .......... 514/1.1; 530/308; 530/400; 514/6.8; 514/6.9; 514/7.2

(58) Field of Classification Search .................. None
See application file for complete search history.

(56) References Cited

U.S. PATENT DOCUMENTS

| | | | |
|---|---|---|---|
| 4,289,689 A | 9/1981 | Friesen et al. |
| 4,738,931 A | 4/1988 | Sugano et al. |
| 4,816,449 A | 3/1989 | Hahn |
| 5,026,651 A | 6/1991 | Bowman et al. |
| 5,091,513 A | 2/1992 | Huston et al. |
| 5,262,177 A | 11/1993 | Brown et al. |
| 5,424,286 A | 6/1995 | Eng |
| 5,432,018 A | 7/1995 | Dower et al. |
| 5,442,043 A | 8/1995 | Fukuta et al. |
| 5,455,030 A | 10/1995 | Ladner et al. |
| 5,464,933 A | 11/1995 | Bolognesi et al. |
| 5,518,889 A | 5/1996 | Ladner et al. |
| 5,545,618 A | 8/1996 | Buckley et al. |
| 5,571,691 A | 11/1996 | Conneely et al. |
| 5,571,896 A | 11/1996 | Conneely et al. |
| 5,656,272 A | 8/1997 | Le et al. |
| 5,672,683 A | 9/1997 | Friden et al. |
| 5,817,789 A | 10/1998 | Heartlein et al. |
| 5,876,969 A | 3/1999 | Fleer et al. |
| 5,925,351 A | 7/1999 | Browning et al. |
| 5,948,613 A | 9/1999 | Teng et al. |
| 5,977,307 A | 11/1999 | Friden et al. |
| 5,986,067 A | 11/1999 | Funk et al. |
| 6,027,921 A | 2/2000 | Heartlein et al. |
| 6,066,469 A | 5/2000 | Kruzel et al. |
| 6,069,193 A | 5/2000 | Vargas et al. |
| 6,191,102 B1 | 2/2001 | DiMarchi et al. |
| 6,245,737 B1 | 6/2001 | Boyd et al. |
| 6,262,026 B1 | 7/2001 | Heartlein et al. |
| 6,277,817 B1 | 8/2001 | Kruzel et al. |
| 6,329,336 B1 | 12/2001 | Bridon et al. |
| 6,348,568 B1 | 2/2002 | Barney et al. |
| 6,380,362 B1 | 4/2002 | Watson et al. |
| 6,420,346 B1 | 7/2002 | Karin |
| 6,455,687 B1 | 9/2002 | Kruzel et al. |
| 6,458,924 B2 | 10/2002 | Knudsen et al. |
| 6,583,111 B1 | 6/2003 | DiMarchi et al. |
| 6,723,530 B1 | 4/2004 | Drucker |
| 6,825,037 B1 | 11/2004 | Funk et al. |
| 6,858,576 B1 | 2/2005 | Young et al. |
| 6,956,026 B2 | 10/2005 | Beeley et al. |
| 6,998,387 B1 | 2/2006 | Goke et al. |
| 7,067,133 B2 | 6/2006 | Nicolau |
| 7,176,278 B2 | 2/2007 | Prior |
| 7,285,526 B2 | 10/2007 | Maroun |
| 2001/0025026 A1 | 9/2001 | Heartlein et al. |
| 2002/0049153 A1 | 4/2002 | Bridon et al. |
| 2003/0199672 A1 | 10/2003 | Knudsen et al. |
| 2003/0226155 A1 | 12/2003 | Sadeghi et al. |
| 2003/0232754 A1 | 12/2003 | Holst et al. |
| 2003/0235884 A1 | 12/2003 | Cummings et al. |
| 2004/0023334 A1 | 2/2004 | Prior |
| 2005/0054043 A1 | 3/2005 | Funk et al. |
| 2006/0105387 A1 | 5/2006 | Prior et al. |
| 2006/0130158 A1 | 6/2006 | Turner et al. |

(Continued)

FOREIGN PATENT DOCUMENTS

EP 0 314 317 5/1989

(Continued)

OTHER PUBLICATIONS

U.S. Appl. No. 11/659,222, filed Aug. 3, 2005. Liu, "International Search Report", from PCT/US05/27800, 4 pages (mailed Apr. 18, 2006).
Helms, "International Search Report", from PCT/US03/26744, 3 pages (mailed Sep. 14, 2005).
Liu, "International Search Report", from PCT/US03/26818, 5 pages (mailed Jul. 14, 2005).
Paras, "International Search Report", from PCT/US02/27637, 3 pages (mailed Feb. 4, 2003).
McGinnis and Foege, "Actual causes of death in the United States", JAMA, 270(18):2207-2212, 1993.
Parkes et al., "Insulinotropic Actions of Exendin-4 and Glucagon-Like Peptide-1 in Vivo and in Vitro", Metabolism, 50 (5):583-589, 2001.
Aziz and Anderson, "Exendin-4, a GLP-1 Receptor Agonist, Modulates the Effect of Macronutrients on Food Intake by Rats", The Journal of Nutrition, 132:990-995, 2002.

(Continued)

*Primary Examiner* — Gyan Chandra

(74) *Attorney, Agent, or Firm* — Martha A. Gammill; Kristina L. Konstas

(57) ABSTRACT

The invention provides fusion proteins comprising an exendin-4 fused to a transferrin (Tf) via a polypeptide linker, as well as corresponding nucleic acid molecules, vectors, host cells, and pharmaceutical compositions. The invention also provides the use of the exendin-4/Tf fusion proteins for treatment of Type II diabetes, obesity, and to reduce body weight.

5 Claims, 4 Drawing Sheets

U.S. PATENT DOCUMENTS

| | | |
|---|---|---|
| 2006/0205037 A1 | 9/2006 | Sadeghi et al. |
| 2007/0060512 A1 | 3/2007 | Sadeghi et al. |

FOREIGN PATENT DOCUMENTS

| | | |
|---|---|---|
| EP | 0 413 662 | 2/1991 |
| EP | 0 978 565 | 2/2000 |
| EP | 1 408 050 | 4/2004 |
| WO | 91/09967 | 7/1991 |
| WO | 95/02421 | 1/1995 |
| WO | 99/43707 | 9/1999 |
| WO | 99/46283 | 9/1999 |
| WO | 00/69911 | 11/2000 |
| WO | 01/04156 | 1/2001 |
| WO | 01/36643 | 5/2001 |
| WO | 01/46254 | 6/2001 |
| WO | 01/79258 | 10/2001 |
| WO | 02/46227 | 6/2002 |
| WO | 03/016349 | 2/2003 |
| WO | 03/020746 | 3/2003 |
| WO | 03/082898 | 10/2003 |
| WO | 2004/019872 | 3/2004 |
| WO | 2004/020404 | 3/2004 |
| WO | 2004/020405 | 3/2004 |
| WO | 2004/020454 | 3/2004 |
| WO | 2004/020588 | 3/2004 |
| WO | 2004/078777 | 9/2004 |
| WO | 2005/021579 | 3/2005 |
| WO | 2006/017688 | 2/2006 |
| WO | 2006/049983 | 5/2006 |
| WO | 2006/096515 | 9/2006 |

OTHER PUBLICATIONS

Egan et al., "The Insulinotropic Effect of Acute Exendin-4 Administered to Humans: Comparison of Nondiabetic State to Type 2 Diabetes", The Journal of Clinical Endocrinology & Metabolism, 87(3):1282-1290, 2002.

Kolterman et al., "Synthetic Exendin-4 (Exenatide) Significantly Reduces Postprandial and Fasting Plasma Glucose in Subjects with Type 2 Diabetes", The Journal of Clinical Endocrinology & Metabolism, 88(7):3082-3089, 2003.

Fineman et al., "Effect on Glycemic Control of Exenatide (Synthetic Exendin-4) Additive to Existing Metformin and/or Sulfonylurea Treatment in Patients With Type 2 Diabetes", Diabetes Care, 26(8):2370-2377, 2003.

PCT International Search Report, PCT/IB2007/002047, 2007.

Egan et al., "Glucagon-like peptide-1, fused to human transferrin, is a long-acting and potent anti-hyperglycemic agent", Diabetologia, 48(Suppl.1):A202, 2005, abstract 548.

Arndt, "Carbohydrate-deficient Transferrin as a Marker of Chronic Alcohol Abuse: A Critical Review of Preanalysis, Analysis, and Interpretation", Clinical Chemistry, 47(1):13-27, 2001.

Ali et al., "Transferrin Trojan Horses as a Rational Approach for the Biological Delivery of Therapeutic Peptide Domains", J. Biol. Chem., 274(34):24066-24073, 1999.

Newton et al., "Antitransferrin receptor antibody-RNase fusion protein expressed in the mammary gland of transgenic mice", Journal of Immunological Methods, 231:159-167, 1999.

Park et al., "Production and Characterization of Fusion Proteins Containing Transferrin and Nerve Growth Factor", Journal of Drug Targeting, 6(1):53-64, 1998.

Prince et al., "Efficient Endocytosis of the Cystic Fibrosis Transmembrane Conductance Regulator Requires a Tyrosine-based Signal", The Journal of Biological Chemistry, 274(6):3602-3609, 1999.

Regoeczi et al., "Rat Aglycotransferrin and Human Monoglycotransferrin: Production and Metabolic Properties", Archives of Biochemistry and Biophysics, 268(2):637-642, 1989.

Shin et al., "Transferrin-antibody fusion proteins are effective in brain targeting", Proc. Natl. Acad. Sci. USA, 92 (7):2820-2824, 1995.

Xia et al., "Hypoglycemic Effect of Insulin-Transferrin Conjugate in Streptozotocin-Induced Diabetic Rats", The Journal of Pharmacology and Experimental Therapeutics, 295(2):594-600, 2000.

Database A_GENESEQ (Compugen Ltd), Accession No. AAR66492, (Jacobs et al), Nov. 25, 1994.

Gallwitz et al., "GLP-1/GIP chimeric peptides define the structural requirements for specific ligand-receptor interaction of GLP-1", Regulatory Peptides, 63(1):17-22, 1996.

Aldred et al., "Synthesis of rat transferrin in Escherichia coli containing a recombinant bacteriophage", Biochemical and Biophysical Research Communications, 122(3):960-965, 1984.

Adrian et al., "Human transferrin. Expression and iron modulation of chimeric genes in transgenic mice", The Journal of Biological Chemistry, 265(22):13344-13350, 1990.

MacGillivray et al., "The Primary Structure of Human Serum Transferrin. The structures of seven cyanogen bromide fragments and the assembly of the complete structure", The Journal of Biological Chemistry, 258 (6):3543-3553, 1983.

Salmon et al., "Production of Human Lactoferrin in Transgenic Tobacco Plants", Protein Expression and Purification, 13:127-135, 1998.

Ward et al., "A System for Production of Commercial Quantities of Human Lactoferrin: A Broad Spectrum Natural Antibiotic", Bio/Technology, 13(5):498-503, 1995.

Gallop et al., "Applications of Combinatorial Technologies to Drug Discovery. 1. Background and Peptide Combinatorial Libraries", J. Med. Chem., 37(9):1233-1251, 1994.

Ali et al., "High-yield production of functionally active human serum transferrin using a baculovirus expression system, and its structural characterization", Biochem. J., 319:191-195, 1996.

Batra et al., "Single-Chain Immunotoxins Directed at the Human Transferrin Receptor Containing Pseudomonas Exotoxin A or Diphtheria Toxin: Anti-TFR(Fv)-PE40 and DT388-Anti-TFR(Fv)", Molecular and Cellular Biology, 11 (4):2200-2205, 1991.

Batra et al., "Recombinant anti-erbB2 immunotoxins containing Pseudomonas exotoxin", Proc. Natl. Acad. Sci. USA, 89(13):5867-5871, 1992.

Bradley and Young, "Anthrax toxin receptor proteins", Biochemical Pharmacology, 65(3):309-314, 2003.

Bradley et al., "Identification of the cellular receptor for anthrax toxin", Nature, 414(6860):225-229, 2001.

Brinkmann et al., "A recombinant immunotoxin that is active on prostate cancer cells and that is composed of the Fv region of monoclonal antibody PR1 and a truncated form of Pseudomonas exotoxin", Proc. Natl. Acad. Sci. USA, 90 (2):547-551, 1993.

Cha et al., "Receptor-Based Antidote for Diphtheria", Infection and Immunity, 70(5):2344-2350, 2002.

Chaudhary et al., "A recombinant immunotoxin consisting of two antibody variable domains fused to Pseudomonas exotoxin", Nature, 339(6223):394-397, 1989.

Deacon et al., "Dipeptidyl peptidase IV resistant analogues of glucagon-like peptide-1 which have extended metabolic stability and improved biological activity", Diabetologia, 41(3):271-278, 1998.

Drucker, "Biological Actions and Therapeutic Potential of the Glucagon-like Peptides", Gastroenterology, 122 (2):531-544, 2002.

Hoefkens et al., "Influence of transferrin glycans on receptor binding and iron-donation", Glycoconjugate Journal, 14 (2):289-295, 1997.

Hoo et al., Characterization of a single-chain T-cell receptor expressed in Escherichia coli, Proc. Natl. Acad. Sci. USA, 89(10):4759-4763, 1992.

Hosoi et al., "Structural Characterization of Fibroblast Human Interferon-betal", Journal of Interferon Research, 8 (3):375-384, 1988.

Huston et al., "Protein engineering of antibody binding sites: Recovery of specific activity in an anti-digoxin single-chain Fv analogue produced in Escherichia coli", Proc. Natl. Acad. Sci. USA, 85(16):5879-5883, 1988.

Johnson et al., "Identification of a 13 Amino Acid Peptide Mimetic of Erythropoietin and Description of Amino Acids Critical for the Mimetic Activity of EMP1", Biochemistry, 37(11):3699-3710, 1998.

Kozaki et al., "Characterization of Clostridium botulinum Type B Neurotoxin Associated with Infant Botulism in Japan", Infection and Immunity, 66(10):4811-4816, 1998.

Li and Singh, "Isolation of synaptotagmin as a receptor for types A and E botulinum neurotoxin and analysis of their comparative binding using a new microtiter plate assay", J Nat Toxins, 7(3):215-226, 1998.

Liang et al., "Production and characterization of monoclonal antibodies against recombinant human tumor necrosis factor/cachectin", Biochem Biophys Res Commun, 137(2):847-854, 1986.

Naglich et al., "Expression Cloning of a Diphtheria Toxin Receptor: Identity with a Heparin-Binding EGF-like Growth Factor Precursor", Cell, 69(6):1051-1061, 1992.

Nicholls et al., "Characterization of Single-chain Antibody (sFv)-Toxin Fusion Proteins produced in vitro in rabbit reticulocyte lysate", J Biol Chem, 268(7):5302-5308, 1993.

Nishiki et al., "Identification of Protein Receptor for *Clostridium botulinum* Type B Neurotoxin in Rat Brain Synaptosomes", The Journal of Biological Chemistry, 269(14):10498-10503, 1994.

O'Harte et al., "NH2-Terminally Modified Gastric Inhibitory Polypeptide Exhibits Amino-Peptidase Resistance and Enhanced Antihyperglycemic Activity", Diabetes, 48(4):758-765, 1999.

Pedersen et al., "Removal of N-Terminal Polyhistidine Tags from Recombinant Proteins Using Engineered Aminopeptidases", Protein Expression and Purification, 15(3):389-400, 1999.

Sheridan et al., "Solid-phase Synthesis and Cyclization of a Large Branched Peptide from IgG Fc with Affinity for Fc gamma RI", Journal of Peptide Science, 5(12):555-562, 1999.

Siegel et al., "Biological activity of GLP-1-analogues with N-terminal modifications", Regulatory Peptides, 79 (2-3):93-102, 1999.

Traunecker et al., "Bispecific single chain molecules (Janusins) target cytotoxic lymphocytes on HIV infected cells", The EMBO Journal, 10(12):3655-3659, 1991.

Wrighton et al., "Small peptides as potent mimetics of the protein hormone erythropoietin", Science, 273 (5274):458-464, 1996.

Xiao et al., "Biological Activities of Glucagon-Like Peptide-1 Analogues in Vitro and in Vivo", Biochemistry, 40 (9):2860-2869, 2001.

Zhao et al., "Inhibition of Dipeptidyl Peptidase IV (DPP IV) by 2-(2-Amino-1-fluoro-propylidene)-cyclopentanecarbonitrile, a Fluoroolefin Containing Peptidomimetic", Bioorganic & Medicinal Chemistry, 11(2):207-215, 2003.

Seffernick et al., "Melamine Deaminase and Atrazine Chlorohydrolase: 98 Percent Identical but Functionally Different", Journal of Bacteriology, 183(8):2405-2410, 2001.

Wells, "Additivity of Mutational Effects in Proteins", Biochemistry, 29(37):8509-8517, 1990.

Sommer, Supplementary Partial European Search Report, from EP 03749159.4, 5 pages, European Patent Office, Munich, Germany (mailed May 30, 2006).

Parise et al., "Construction and in vitro functional evaluation of a low-density lipoprotein receptor/transferrin fusion protein as a therapeutic tool for familial hypercholesterolemia", Human Gene Therapy, 10(7):1219-1228, 1999.

Vogt, "Communication pursuant to Article 96(2) EPC", from EP 02757486.2, 7 pages, European Patent Office, Munich, Germany (mailed Jun. 1, 2006).

Adelhorst et al., "Structure-Activity Studies of Glucagon-like Peptide-1", The Journal of Biological Chemistry, 269 (9):6275-6278, 1994.

Kawai et al., "The Biological Effects of Glucagon-Like Peptide-1 (GLP-1) and its Structure-Activity Relationship", Biomedical Research, 9(Suppl. 3):213-217, 1988.

Kieffer et al., "Degradation of Glucose-Dependent Insulinotropic Polypeptide and Truncated Glucagon-Like Peptide 1 in Vitro and in Vivo by Dipeptidyl Peptidase IV", Endocrinology, 136(8)3585-3596, 1995.

Knudsen et al., "Potent Derivatives of Glucagon-like Peptide-1 with Pharmacokinetic Properties Suitable for Once Daily Administration", J. Med. Chem., 43(9):1664-1669, 2000.

Mojsov, "Structural requirements for biological activity of glucagon-like peptide-I", Int J Pept Protein Res, 40 (3-4):333-343, 1992.

Mossier, "Supplementary Partial European Search Report", from EP 04717362.0, 12 pages, European Patent Office, Munich, Germany (mailed Aug. 8, 2006).

Ohneda et al., "The Structure-Function Relationship of GLP-1 Related Peptides in the Endocrine Function of the Canine Pancreas", Tohoku J. Exp. Med., 165(3):209-221, 1991.

Bennett, "International Search Report", from PCT/US03/26779, 5 pages (mailed Mar. 2, 2005).

Johnson and Jolliffe, "Erythropoietin mimetic peptides and the future", Nephrol Dial Transplant, 15 (9):1274-1277, 2000.

Livnah et al., "Functional Mimicry of a Protein Hormone by a Peptide Agonist: The EPO Receptor Complex at 2.8 Angstrom", Science, 273(5274):464-471, 1996.

Mayer, "International Search Report", from PCT/US04/27949, 5 pages (mailed Jun. 8, 2005).

Mossier, "Partial European Search Report", from EP 03791808.3, 6 pages, European Patent Office, Munich, Germany (mailed Apr. 18, 2006).

Qureshi et al., "Mimicry of erythropoietin by a nonpeptide molecule", Proc. Natl. Acad. Sci. USA, 96:12156-12161, 1999.

Robinson, "International Search Report", from PCT/US03/26742, 4 pages (mailed Sep. 14, 2004).

Ton, "International Search Report", from PCT/US03/26778, 2 pages (mailed Mar. 25, 2004).

Wagner et al., "Delivery of drugs, proteins and genes into cells using transferrin as a ligand for receptor-mediated endocytosis", Adv. Drug. Deliv. Rev., 14:113-135, 1994.

Liu, "International Search Report", from PCT/US06/07617, 6 pages (mailed Sep. 20, 2006).

Amit et al., "Three-Dimensional Structure of an Antigen-Antibody Complex at 2.8 Angstrom Resolution", Science, 233 (4765):747-753, 1986.

Bowie et al., "Deciphering the Message in Protein Sequences: Tolerance to Amino Acid Substitutions", Science, 247:1306-1310, 1990.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cellular Biology, 111(5 Pt 1):2129-2138, 1990.

Carlson, "International Search Report", from PCT/US05/38531, 2 pages (mailed Oct. 19, 2006).

Duksin and Mahoney, "Relationship of the Structure and Biological Activity of the Natural Homologues of Tunicamycin", The Journal of Biological Chemistry, 257(6):3105-3109, 1982.

Eigler et al., "Taming TNF: strategies to restrain this proinflammatory cytokine", Immunology Today, 18(10):487-492, 1997.

Holliger et al., ""Diabodies": Small bivalent and bispecific antibody fragments", Proc. Natl. Acad. Sci. USA, 90 (14):6444-6448, 1993.

Lazar et al., "Transforming Growth Factor alpha: Mutation of Aspartic Acid 47 and Leucine 48 Results in Different Biological Activities", Molecular and Cellular Biology, 8(3):1247-1252, 1988.

Li and Qian, "Transferrin/Transferrin Receptor-Mediated Drug Delivery", Medicinal Research Reviews, 22(3):225-250, 2002.

Liu, "International Search Report", from PCT/US04/06462, 7 pages (mailed Nov. 15, 2005).

Liu, "PCT Written Opinion", from PCT/US03/26818 (mailed Oct. 19, 2006).

Ngo et al., "Computational Complexity, Protein Structure Prediction, and the Levinthal Paradox", in The Protein Folding Problem and Tertiary Structure Prediction, Merz et al. (Eds.), Birkhauser, Boston, MA, pp. 433 and 492-495, 1994.

Panka et al., "Variable region framework differences result in decreased or increased affinity of variant anti-digoxin antibodies", Proc. Natl. Acad. Sci. USA, 85(9):3080-3084, 1988.

Parker et al., "Agonist internalization by cloned Y1 neuropeptide Y (NPY) receptor in Chinese hamster ovary cells shows strong preference for NPY, endosome-linked entry and fast receptor recycling", Regulatory Peptides, 107:49-62, 2002.

Rudikoff et al., "Single amino acid substitution altering antigen-binding specificity", Proc. Natl. Acad. Sci. USA, 79 (6):1979-1983, 1982.

Skolnick and Fetrow, "From genes to protein structure and function: novel applications of computational approaches in the genomic era", Trends Biotechnol., 18(1):34-39, 2000.

Vogt, "Supplementary European Search Report", from EP 02757486.2, 2 pages, European Patent Office, Munich, Germany (mailed Dec. 6, 2005).

Penichet et al., "An Antibody-Avidin Fusion Protein Specific for the Transferrin Receptor Serves as a Delivery Vehicle for Effective Brain Targeting: Initial Applications in Anti-HIV Antisense Drug Delivery to the Brain", Journal of Immunology, 163(8):4421-4426, 1999.

SEQUENCE LISTING

```
<160> NUMBER OF SEQ ID NOS: 47

<210> SEQ ID NO 1
<211> LENGTH: 2318
<212> TYPE: DNA
<213> ORGANISM: Homo sapiens

<400> SEQUENCE: 1
gcacagaagc gagtccgact gtgctcgctg ctcagcgccg cacccggaag atgaggctcg      60
ccgtgggagc cctgctggtc tgcgccgtcc tggggctgtg tctggctgtc cctgataaaa     120
ctgtgagatg gtgtgcagtg tcggagcatg aggccactaa gtgccagagt ttccgcgacc     180
atatgaaaag cgtcattcca tccgatggtc ccagtgttgc ttgtgtgaag aaagcctcct     240
accttgattg catcagggcc attgcggcaa acgaagcgga tgctgtgaca ctggatgcag     300
gtttggtgta tgatgcttac ctggctccca taaacctgaa gcctgtggtg gcagagttct     360
atgggtcaaa agaggatcca cagactttct attatgctgt tgctgtggtg aagaaggata     420
gtggcttcca gatgaaccag cttcgaggca agaagtcctg ccacacgggt ctaggcaggt     480
ccgctgggtg gaacatcccc ataggcttac tttactgtga cttacctgag ccacgtaaac     540
ctcttgagaa agcagtggcc aatttcttct cgggcagctg tgcccttgt gcggatggga     600 cggacttccc ccagctgtgt caactgtgtc cagggtgtgg ctgctccacc cttaaccaat     660
acttcggcta ctcgggagcc ttcaagtgtc tgaaggatgg tgctggggat gtggccttg     720 tcaagcactc gactatattt gagaacttgg caaacaaggc tgacagggac cagtatgagc     780
tgctttgcct ggacaacacc cggaagccgg tagatgaata caaggactgc cacttggccc     840
aggtcccttc tcataccgtc gtggcccgaa gtatgggcgg caaggaggac ttgatctggg     900
```

```
agcttctcaa ccaggcccag gaacattttg gcaaagacaa atcaaaagaa ttccaactat    960
tcagctctcc tcatgggaag gacctgctgt ttaaggactc tgcccacggg tttttaaaag   1020
tcccccccag gatggatgcc aagatgtacc tgggctatga gtatgtcact gccatccgga   1080
atctacggga aggcacatgc ccagaagccc aacagatga atgcaagcct gtgaagtggt   1140
gtgcgctgag ccaccacgag aggctcaagt gtgatgagtg gagtgttaac agtgtaggga   1200
aaatagagtg tgtatcagca gagaccaccg aagactgcat cgccaagatc atgaatggag   1260
aagctgatgc catgagcttg gatggagggt ttgtctacat agcgggcaag tgtggtctgg   1320
tgcctgtctt ggcagaaaac tacaataaga gcgataattg tgaggataca ccagaggcag   1380
ggtattttgc tgtagcagtg gtgaagaaat cagcttctga cctcacctgg gacaatctga   1440
aaggcaagaa gtcctgccat acggcagttg gcagaaccgc tggctggaac atccccatgg   1500
gcctgctcta caataagatc aaccactgca gatttgatga atttttcagt gaaggttgtg   1560
cccctgggtc taagaaagac tccagtctct gtaagctgtg tatgggctca ggcctaaacc   1620
tgtgtgaacc caacaacaaa gagggatact acggctacac aggcgctttc aggtgtctgg   1680
ttgagaaggg agatgtggcc tttgtgaaac ccagactgt cccacagaac actgggggaa   1740
aaaaccctga tccatgggct aagaatctga atgaaaaaga ctatgagttg ctgtgccttg   1800
atggtaccag gaaacctgtg gaggagtatg cgaactgcca cctggccaga gccccgaatc   1860
acgctgtggt cacacggaaa gataaggaag cttgcgtcca caagatatta cgtcaacagc   1920
agcacctatt tggaagcaac gtaactgact gctcgggcaa cttttgtttg ttccggtcgg   1980
aaaccaagga cccttctgttc agagatgaca cagtatgttt ggccaaactt catgacagaa   2040
acacatatga aaatactta ggagaagaat atgtcaaggc tgttggtaac ctgagaaaat   2100
gctccacctc atcactcctg gaagcctgca ctttccgtag accttaaaat ctcagaggta   2160
gggctgccac caaggtgaag atgggaacgc agatgatcca tgagtttgcc ctggtttcac   2220
tggcccaagt ggtttgtgct aaccacgtct gtcttcacag ctctgtgttg ccatgtgtgc   2280
tgaacaaaaa ataaaaatta ttattgattt tatattttc                         2318
```

<210> SEQ ID NO 2
<211> LENGTH: 698
<212> TYPE: PRT
<213> ORGANISM: Homo sapiens

<400> SEQUENCE: 2

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125
```

```
Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
                180                 185                 190

Cys Pro Gly Cys Gly Cys Ser Thr Leu Asn Gln Tyr Phe Gly Tyr Ser
            195                 200                 205

Gly Ala Phe Lys Cys Leu Lys Asp Gly Ala Gly Asp Val Ala Phe Val
        210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
                260                 265                 270

Arg Ser Met Gly Gly Lys Glu Asp Leu Ile Trp Glu Leu Leu Asn Gln
            275                 280                 285

Ala Gln Glu His Phe Gly Lys Asp Lys Ser Lys Glu Phe Gln Leu Phe
        290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
                340                 345                 350

Ala Pro Thr Asp Glu Cys Lys Pro Val Lys Trp Cys Ala Leu Ser His
            355                 360                 365

His Glu Arg Leu Lys Cys Asp Glu Trp Ser Val Asn Ser Val Gly Lys
        370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
                420                 425                 430

Lys Ser Asp Asn Cys Glu Asp Thr Pro Glu Ala Gly Tyr Phe Ala Val
            435                 440                 445

Ala Val Val Lys Lys Ser Ala Ser Asp Leu Thr Trp Asp Asn Leu Lys
        450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
            515                 520                 525

Asn Lys Glu Gly Tyr Tyr Gly Tyr Thr Gly Ala Phe Arg Cys Leu Val
        530                 535                 540

Glu Lys Gly Asp Val Ala Phe Val Lys His Gln Thr Val Pro Gln Asn
545                 550                 555                 560
```

```
Thr Gly Gly Lys Asn Pro Asp Pro Trp Ala Lys Asn Leu Asn Glu Lys
            565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
            595                 600                 605

Arg Lys Asp Lys Glu Ala Cys Val His Lys Ile Leu Arg Gln Gln Gln
        610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
            675                 680                 685

Leu Leu Glu Ala Cys Thr Phe Arg Arg Pro
        690                 695

<210> SEQ ID NO 3
<211> LENGTH: 679
<212> TYPE: PRT
<213> ORGANISM: Homo sapiens

<400> SEQUENCE: 3

Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
    50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Tyr
                85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
        115                 120                 125

Asn Ile Pro Ile Gly Leu Leu Tyr Cys Asp Leu Pro Glu Pro Arg Lys
    130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
        195                 200                 205

Thr Ile Phe Glu Asn Leu Ala Asn Lys Ala Asp Arg Asp Gln Tyr Glu
    210                 215                 220

Leu Leu Cys Leu Asp Asn Thr Arg Lys Pro Val Asp Glu Tyr Lys Asp
225                 230                 235                 240
```

```
Cys His Leu Ala Gln Val Pro Ser His Thr Val Ala Arg Ser Met
            245                 250                 255
Gly Gly Lys Glu Asp Leu Ile Trp Glu Leu Leu Asn Gln Ala Gln Glu
        260                 265                 270
His Phe Gly Lys Asp Lys Ser Lys Glu Phe Gln Leu Phe Ser Ser Pro
            275                 280                 285
His Gly Lys Asp Leu Leu Phe Lys Asp Ser Ala His Gly Phe Leu Lys
        290                 295                 300
Val Pro Pro Arg Met Asp Ala Lys Met Tyr Leu Gly Tyr Glu Tyr Val
305                 310                 315                 320
Thr Ala Ile Arg Asn Leu Arg Glu Gly Thr Cys Pro Glu Ala Pro Thr
                325                 330                 335
Asp Glu Cys Lys Pro Val Lys Trp Cys Ala Leu Ser His His Glu Arg
            340                 345                 350
Leu Lys Cys Asp Glu Trp Ser Val Asn Ser Val Gly Lys Ile Glu Cys
        355                 360                 365
Val Ser Ala Glu Thr Thr Glu Asp Cys Ile Ala Lys Ile Met Asn Gly
    370                 375                 380
Glu Ala Asp Ala Met Ser Leu Asp Gly Gly Phe Val Tyr Ile Ala Gly
385                 390                 395                 400
Lys Cys Gly Leu Val Pro Val Leu Ala Glu Asn Tyr Asn Lys Ser Asp
                405                 410                 415
Asn Cys Glu Asp Thr Pro Glu Ala Gly Tyr Phe Ala Val Ala Val Val
            420                 425                 430
Lys Lys Ser Ala Ser Asp Leu Thr Trp Asp Asn Leu Lys Gly Lys Lys
        435                 440                 445
Ser Cys His Thr Ala Val Gly Arg Thr Ala Gly Trp Asn Ile Pro Met
    450                 455                 460
Gly Leu Leu Tyr Asn Lys Ile Asn His Cys Arg Phe Asp Glu Phe Phe
465                 470                 475                 480
Ser Glu Gly Cys Ala Pro Gly Ser Lys Lys Asp Ser Ser Leu Cys Lys
                485                 490                 495
Leu Cys Met Gly Ser Gly Leu Asn Leu Cys Glu Pro Asn Asn Lys Glu
            500                 505                 510
Gly Tyr Tyr Gly Tyr Thr Gly Ala Phe Arg Cys Leu Val Glu Lys Gly
        515                 520                 525
Asp Val Ala Phe Val Lys His Gln Thr Val Pro Gln Asn Thr Gly Gly
    530                 535                 540
Lys Asn Pro Asp Pro Trp Ala Lys Asn Leu Asn Glu Lys Asp Tyr Glu
545                 550                 555                 560
Leu Leu Cys Leu Asp Gly Thr Arg Lys Pro Val Glu Glu Tyr Ala Asn
                565                 570                 575
Cys His Leu Ala Arg Ala Pro Asn His Ala Val Val Thr Arg Lys Asp
            580                 585                 590
Lys Glu Ala Cys Val His Lys Ile Leu Arg Gln Gln Gln His Leu Phe
        595                 600                 605
Gly Ser Asn Val Thr Asp Cys Ser Gly Asn Phe Cys Leu Phe Arg Ser
    610                 615                 620
Glu Thr Lys Asp Leu Leu Phe Arg Asp Asp Thr Val Cys Leu Ala Lys
625                 630                 635                 640
Leu His Asp Arg Asn Thr Tyr Glu Lys Tyr Leu Gly Glu Glu Tyr Val
                645                 650                 655
Lys Ala Val Gly Asn Leu Arg Lys Cys Ser Thr Ser Ser Leu Leu Glu
```

```
                    660                 665                 670
Ala Cys Thr Phe Arg Arg Pro
        675

<210> SEQ ID NO 4
<211> LENGTH: 39
<212> TYPE: PRT
<213> ORGANISM: Heloderma suspectum

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 12
<212> TYPE: PRT
<213> ORGANISM: Unknown
<220> FEATURE:
<223> OTHER INFORMATION: linker peptide

<400> SEQUENCE: 5

Pro Glu Ala Pro Thr Asp Pro Glu Ala Pro Thr Asp
1               5                   10

<210> SEQ ID NO 6
<211> LENGTH: 6
<212> TYPE: PRT
<213> ORGANISM: Artificial Sequence
<220> FEATURE:
<223> OTHER INFORMATION: non-helical linker peptide

<400> SEQUENCE: 6

Pro Glu Ala Pro Thr Asp
1               5

<210> SEQ ID NO 7
<211> LENGTH: 16
<212> TYPE: PRT
<213> ORGANISM: Artificial Sequence
<220> FEATURE:
<223> OTHER INFORMATION: peptide linker

<400> SEQUENCE: 7

Pro Glu Ala Pro Thr Asp Glu Pro Lys Ser Cys Asp Lys Thr His Thr
1               5                   10                  15

<210> SEQ ID NO 8
<211> LENGTH: 31
<212> TYPE: PRT
<213> ORGANISM: Artificial Sequence
<220> FEATURE:
<223> OTHER INFORMATION: peptide linker

<400> SEQUENCE: 8

Pro Glu Ala Pro Thr Asp Val Glu Pro Lys Ser Ser Asp Lys Thr His
1               5                   10                  15

Thr Ser Pro Pro Ser Pro Ala Pro Glu Leu Leu Gly Gly Pro Ser
            20                  25                  30

<210> SEQ ID NO 9
<211> LENGTH: 31
```

```
<212> TYPE: PRT
<213> ORGANISM: Artificial Sequence
<220> FEATURE:
<223> OTHER INFORMATION: peptide linker

<400> SEQUENCE: 9

Pro Glu Ala Pro Thr Asp Val Glu Pro Lys Ser Ala Asp Lys Thr His
1               5                   10                  15

Thr Ala Pro Pro Ala Pro Ala Pro Glu Leu Leu Gly Gly Pro Ser
            20                  25                  30

<210> SEQ ID NO 10
<211> LENGTH: 21
<212> TYPE: PRT
<213> ORGANISM: Artificial Sequence
<220> FEATURE:
<223> OTHER INFORMATION: peptide linker

<400> SEQUENCE: 10

Glu Pro Lys Ser Cys Asp Lys Thr His Thr Cys Pro Pro Cys Pro Pro
1               5                   10                  15

Glu Ala Pro Thr Asp
            20

<210> SEQ ID NO 11
<211> LENGTH: 31
<212> TYPE: PRT
<213> ORGANISM: Artificial Sequence
<220> FEATURE:
<223> OTHER INFORMATION: peptide linker

<400> SEQUENCE: 11

Val Glu Pro Lys Ser Ser Asp Lys Thr His Thr Ser Pro Pro Ser Pro
1               5                   10                  15

Ala Pro Glu Leu Leu Gly Gly Pro Ser Pro Glu Ala Pro Thr Asp
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: peptide linker

<400> SEQUENCE: 12

Val Glu Pro Lys Ser Ala Asp Lys Thr His Thr Ala Pro Pro Ala Pro
1               5                   10                  15

Ala Pro Glu Leu Leu Gly Gly Pro Ser Pro Glu Ala Pro Thr Asp
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: peptide linker

<400> SEQUENCE: 13

Pro Glu Ala Pro Thr Asp Val Glu Pro Lys Ser Cys Asp Lys Thr His
1               5                   10                  15

Thr Cys Pro Pro Cys Pro Ala Pro Glu Leu Leu Gly Gly Pro Ser
            20                  25                  30

<210> SEQ ID NO 14
<211> LENGTH: 31
```

<210> SEQ ID NO 14
<211> LENGTH: (not shown)
<212> TYPE: PRT
<213> ORGANISM: Artificial Sequence
<220> FEATURE:
<223> OTHER INFORMATION: peptide linker

<400> SEQUENCE: 14

```
Val Glu Pro Lys Ser Cys Asp Lys Thr His Thr Cys Pro Pro Cys Pro
1               5                   10                  15
Ala Pro Glu Leu Leu Gly Gly Pro Ser Pro Glu Ala Pro Thr Asp
            20                  25                  30
```

<210> SEQ ID NO 15
<211> LENGTH: 31
<212> TYPE: PRT
<213> ORGANISM: Artificial Sequence
<220> FEATURE:
<223> OTHER INFORMATION: peptide linker

<400> SEQUENCE: 15

```
Pro Glu Ala Pro Thr Asp Val Glu Pro Lys Ala Ala Asp Lys Thr His
1               5                   10                  15
Thr Ala Pro Pro Ala Pro Ala Pro Glu Leu Leu Gly Gly Pro Ala
            20                  25                  30
```

<210> SEQ ID NO 16
<211> LENGTH: 31
<212> TYPE: PRT
<213> ORGANISM: Artificial Sequence
<220> FEATURE:
<223> OTHER INFORMATION: peptide linker

<400> SEQUENCE: 16

```
Val Glu Pro Lys Ala Ala Asp Lys Thr His Thr Ala Pro Pro Ala Pro
1               5                   10                  15
Ala Pro Glu Leu Leu Gly Gly Pro Ala Pro Glu Ala Pro Thr Asp
            20                  25                  30
```

<210> SEQ ID NO 17
<211> LENGTH: 679
<212> TYPE: PRT
<213> ORGANISM: Homo sapiens

<400> SEQUENCE: 17

```
Val Pro Asp Lys Thr Val Arg Trp Cys Ala Val Ser Glu His Glu Ala
1               5                   10                  15
Thr Lys Cys Gln Ser Phe Arg Asp His Met Lys Ser Val Ile Pro Ser
            20                  25                  30
Asp Gly Pro Ser Val Ala Cys Val Lys Lys Ala Ser Tyr Leu Asp Cys
        35                  40                  45
Ile Arg Ala Ile Ala Ala Asn Glu Ala Asp Ala Val Thr Leu Asp Ala
    50                  55                  60
Gly Leu Val Tyr Asp Ala Tyr Leu Ala Pro Asn Asn Leu Lys Pro Val
65                  70                  75                  80
Val Ala Glu Phe Tyr Gly Ser Lys Glu Asp Pro Gln Thr Phe Tyr Tyr
                85                  90                  95
Ala Val Ala Val Val Lys Lys Asp Ser Gly Phe Gln Met Asn Gln Leu
            100                 105                 110
Arg Gly Lys Lys Ser Cys His Thr Gly Leu Gly Arg Ser Ala Gly Trp
        115                 120                 125
Asn Ile Pro Ile Gly Leu Leu Tyr Cys Asp Leu Pro Glu Pro Arg Lys
    130                 135                 140
```

-continued

```
Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
            165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
            195                 200                 205

Thr Ile Phe Glu Asn Leu Ala Asn Lys Ala Asp Arg Asp Gln Tyr Glu
210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
            245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
            275                 280                 285

His Gly Lys Asp Leu Leu Phe Lys Asp Ser Ala His Gly Phe Leu Lys
            290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
            325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
            355                 360                 365

Val Ser Ala Glu Thr Thr Glu Asp Cys Ile Ala Lys Ile Met Asn Gly
370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ala Asp
            405                 410                 415

Asn Cys Glu Asp Thr Pro Glu Ala Gly Tyr Phe Ala Val Ala Val Val
            420                 425                 430

Lys Lys Ser Ala Ser Asp Leu Thr Trp Asp Asn Leu Lys Gly Lys Lys
            435                 440                 445

Ser Cys His Thr Ala Val Gly Arg Thr Ala Gly Trp Asn Ile Pro Met
450                 455                 460

Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
            485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
            515                 520                 525

Asp Val Ala Phe Val Lys His Gln Thr Val Pro Gln Asn Thr Gly Gly
            530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
            565                 570                 575
```

```
Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
        595                 600                 605

Gly Ser Asn Val Ala Asp Cys Ser Gly Asn Phe Cys Leu Phe Arg Ser
    610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Tyr Val
                645                 650                 655

Lys Ala Val Gly Asn Leu Arg Lys Cys Ser Thr Ser Ser Leu Leu Glu
        660                 665                 670

Ala Cys Thr Phe Arg Arg Pro
        675

<210> SEQ ID NO 18
<211> LENGTH: 19
<212> TYPE: PRT
<213> ORGANISM: Homo sapiens

<400> SEQUENCE: 18

Met Arg Leu Ala Val Gly Ala Leu Leu Val Cys Ala Val Leu Gly Leu
1               5                   10                  15

Cys Leu Ala

<210> SEQ ID NO 19
<211> LENGTH: 57
<212> TYPE: DNA
<213> ORGANISM: Homo sapiens

<400> SEQUENCE: 19
atgaggctcg ccgtgggagc cctgctggtc tgcgccgtcc tggggctgtg tctggcg      57

<210> SEQ ID NO 20
<211> LENGTH: 117
<212> TYPE: DNA
<213> ORGANISM: Heloderma suspectum

<400> SEQUENCE: 20
catggtgaag gtacttttac ttctgatttg tctaaacaaa tggaagaaga agctgttaga     60
ttgtttattg aatggttgaa aaatggtggt ccatcttctg gtgctccacc accatct      117

<210> SEQ ID NO 21
<211> LENGTH: 36
<212> TYPE: DNA
<213> ORGANISM: Artificial Sequence
<220> FEATURE:
<223> OTHER INFORMATION: encodes protein of SEQ ID NO:5

<400> SEQUENCE: 21
ccagaagctc aactgatcc agaagctcca actgat                               36

<210> SEQ ID NO 22
<211> LENGTH: 2043
<212> TYPE: DNA
<213> ORGANISM: Homo sapiens

<400> SEQUENCE: 22
gtacctgata aaactgtgag atggtgtgca gtgtcggagc atgaggccac taagtgccag     60
agtttccgcg accatatgaa aagcgtcatt ccatccgatg gtcccagtgt tgcttgtgtg    120
```

```
aagaaagcct cctaccttga ttgcatcagg gccattgcgg caaacgaagc ggatgctgtg    180
acactggatg caggtttggt gtatgatgct tacctggctc ccaataacct gaagcctgtg    240
gtggcagagt tctatgggtc aaaagaggat ccacagactt tctattatgc tgttgctgtg    300
gtgaagaagg atagtggctt ccagatgaac cagcttcgag caagaagtc ctgccacacg     360 ggtctaggca ggtccgctgg gtggaacatc cccataggct tactttactg tgacttacct    420
gagccacgta aacctcttga gaaagcagtg gccaatttct tctcgggcag ctgtgcccct    480
tgtgcggatg ggacggactt cccccagctg tgtcaactgt gtccagggtg tggctgctcc    540
acccttaacc aatacttcgg ctactcggga gccttcaagt gtctgaagga tggtgctggg    600
gatgtggcct ttgtcaagca ctcgactata tttgagaact tggcaaacaa ggctgacagg    660
gaccagtatg agctgctttg cctggacaac acccggaagc cggtagatga atacaaggac    720
tgccacttgg cccaggtccc ttctcatacc gtcgtggccc gaagtatggg cggcaaggag    780
gacttgatct gggagcttct caaccaggcc caggaacatt ttggcaaaga caatcaaaa     840 gaattccaac tattcagctc tcctcatggg aaggacctgc tgtttaagga ctctgcccac    900
gggtttttaa aagtcccccc caggatggat gccaagatgt acctgggcta tgagtatgtc    960
actgccatcc ggaatctacg ggaaggcaca tgcccagaag ccccaacaga tgaatgcaag   1020
cctgtgaagt ggtgtgcgct gagccaccac gagaggctca agtgtgatga gtggagtgtt   1080
aacagtgtag ggaaaataga gtgtgtatca gcagagacca ccgaagactg catcgccaag   1140
atcatgaatg gagaagctga tgccatgagc ttggatggag ggtttgtcta catagcgggc   1200
aagtgtggtc tggtgcctgt cttggcagaa aactacaata aggctgataa ttgtgaggat   1260
acaccagagg cagggtattt tgctgtagca gtggtgaaga aatcagcttc tgacctcacc   1320
tgggacaatc tgaaaggcaa gaagtcctgc catacggcag ttgcagaaac cgctggctgg   1380
aacatcccca tgggcctgct ctacaataag atcaaccact gcagatttga tgaattttc    1440 agtgaaggtt gtgcccctgg gtctaagaaa gactccagtc tctgtaagct gtgtatgggc   1500
tcaggcctaa acctctgtga acccaacaac aaagagggat actacggcta cacaggcgct   1560
ttcaggtgtc tggttgagaa gggagatgtg gcctttgtga acaccagac tgtcccacag    1620 aacactgggg gaaaaaccc tgatccatgg gctaagaatc tgaatgaaaa agactatgag    1680
ttgctgtgcc ttgatggtac taggaaacct gtggaggagt atgcgaactg ccacctggcc    1740 agagcccga atcacgctgt ggtcacacg aaagataagg aagcatgcgt ccacaagata     1800
ttacgtcaac agcagcacct atttggaagc aacgtagctg actgctcggg caacttttgt   1860
ttgttccggt cggaaaccaa ggaccttctg ttcagagatg acacagtatg tttggccaaa   1920
cttcatgaca gaaacacata tgaaaaatac ttaggagaag aatatgtcaa ggctgttggt   1980
aacctgagaa aatgctccac ctcatcactc ctggaagcct gcactttccg tcgaccttaa   2040
taa                                                                  2043
```

<210> SEQ ID NO 23
<211> LENGTH: 730
<212> TYPE: PRT
<213> ORGANISM: Artificial Sequence
<220> FEATURE:
<223> OTHER INFORMATION: Heloderma suspectum homo sapien

<400> SEQUENCE: 23

His Gly Glu Gly Thr Phe Thr Ser Asp Leu Ser Lys Gln Met Glu Glu
1               5                   10                  15

```
Glu Ala Val Arg Leu Phe Ile Glu Trp Leu Lys Asn Gly Gly Pro Ser
             20                  25                  30

Ser Gly Ala Pro Pro Ser Pro Glu Ala Pro Thr Asp Pro Glu Ala
         35                  40                  45

Pro Thr Asp Val Pro Asp Lys Thr Val Arg Trp Cys Ala Val Ser Glu
 50                  55                  60

His Glu Ala Thr Lys Cys Gln Ser Phe Arg Asp His Met Lys Ser Val
 65                  70                  75                  80

Ile Pro Ser Asp Gly Pro Ser Val Ala Cys Val Lys Lys Ala Ser Tyr
                 85                  90                  95

Leu Asp Cys Ile Arg Ala Ile Ala Ala Asn Glu Ala Asp Ala Val Thr
                100                 105                 110

Leu Asp Ala Gly Leu Val Tyr Asp Ala Tyr Leu Ala Pro Asn Asn Leu
            115                 120                 125

Lys Pro Val Val Ala Glu Phe Tyr Gly Ser Lys Glu Asp Pro Gln Thr
        130                 135                 140

Phe Tyr Tyr Ala Val Ala Val Val Lys Lys Asp Ser Gly Phe Gln Met
145                 150                 155                 160

Asn Gln Leu Arg Gly Lys Lys Ser Cys His Thr Gly Leu Gly Arg Ser
                165                 170                 175

Ala Gly Trp Asn Ile Pro Ile Gly Leu Leu Tyr Cys Asp Leu Pro Glu
            180                 185                 190

Pro Arg Lys Pro Leu Glu Lys Ala Val Ala Asn Phe Phe Ser Gly Ser
        195                 200                 205

Cys Ala Pro Cys Ala Asp Gly Thr Asp Phe Pro Gln Leu Cys Gln Leu
    210                 215                 220

Cys Pro Gly Cys Gly Cys Ser Thr Leu Asn Gln Tyr Phe Gly Tyr Ser
225                 230                 235                 240

Gly Ala Phe Lys Cys Leu Lys Asp Gly Ala Gly Asp Val Ala Phe Val
                245                 250                 255

Lys His Ser Thr Ile Phe Glu Asn Leu Ala Asn Lys Ala Asp Arg Asp
            260                 265                 270

Gln Tyr Glu Leu Leu Cys Leu Asp Asn Thr Arg Lys Pro Val Asp Glu
        275                 280                 285

Tyr Lys Asp Cys His Leu Ala Gln Val Pro Ser His Thr Val Val Ala
    290                 295                 300

Arg Ser Met Gly Gly Lys Glu Asp Leu Ile Trp Glu Leu Leu Asn Gln
305                 310                 315                 320

Ala Gln Glu His Phe Gly Lys Asp Lys Ser Lys Glu Phe Gln Leu Phe
                325                 330                 335

Ser Ser Pro His Gly Lys Asp Leu Leu Phe Lys Asp Ser Ala His Gly
            340                 345                 350

Phe Leu Lys Val Pro Pro Arg Met Asp Ala Lys Met Tyr Leu Gly Tyr
        355                 360                 365

Glu Tyr Val Thr Ala Ile Arg Asn Leu Arg Glu Gly Thr Cys Pro Glu
    370                 375                 380

Ala Pro Thr Asp Glu Cys Lys Pro Val Lys Trp Cys Ala Leu Ser His
385                 390                 395                 400

His Glu Arg Leu Lys Cys Asp Glu Trp Ser Val Asn Ser Val Gly Lys
                405                 410                 415

Ile Glu Cys Val Ser Ala Glu Thr Thr Glu Asp Cys Ile Ala Lys Ile
            420                 425                 430

Met Asn Gly Glu Ala Asp Ala Met Ser Leu Asp Gly Gly Phe Val Tyr
        435                 440                 445
```

Ile Ala Gly Lys Cys Gly Leu Val Pro Val Leu Ala Glu Asn Tyr Asn
450                 455                 460

Lys Ala Asp Asn Cys Glu Asp Thr Pro Glu Ala Gly Tyr Phe Ala Val
465                 470                 475                 480

Ala Val Val Lys Lys Ser Ala Ser Asp Leu Thr Trp Asp Asn Leu Lys
            485                 490                 495

Gly Lys Lys Ser Cys His Thr Ala Val Gly Arg Thr Ala Gly Trp Asn
            500                 505                 510

Ile Pro Met Gly Leu Leu Tyr Asn Lys Ile Asn His Cys Arg Phe Asp
        515                 520                 525

Glu Phe Phe Ser Glu Gly Cys Ala Pro Gly Ser Lys Lys Asp Ser Ser
        530                 535                 540

Leu Cys Lys Leu Cys Met Gly Ser Gly Leu Asn Leu Cys Glu Pro Asn
545                 550                 555                 560

Asn Lys Glu Gly Tyr Tyr Gly Tyr Thr Gly Ala Phe Arg Cys Leu Val
                565                 570                 575

Glu Lys Gly Asp Val Ala Phe Val Lys His Gln Thr Val Pro Gln Asn
            580                 585                 590

Thr Gly Gly Lys Asn Pro Asp Pro Trp Ala Lys Asn Leu Asn Glu Lys
            595                 600                 605

Asp Tyr Glu Leu Leu Cys Leu Asp Gly Thr Arg Lys Pro Val Glu Glu
610                 615                 620

Tyr Ala Asn Cys His Leu Ala Arg Ala Pro Asn His Ala Val Val Thr
625                 630                 635                 640

Arg Lys Asp Lys Glu Ala Cys Val His Lys Ile Leu Arg Gln Gln Gln
                645                 650                 655

His Leu Phe Gly Ser Asn Val Ala Asp Cys Ser Gly Asn Phe Cys Leu
            660                 665                 670

Phe Arg Ser Glu Thr Lys Asp Leu Leu Phe Arg Asp Asp Thr Val Cys
        675                 680                 685

Leu Ala Lys Leu His Asp Arg Asn Thr Tyr Glu Lys Tyr Leu Gly Glu
        690                 695                 700

Glu Tyr Val Lys Ala Val Gly Asn Leu Arg Lys Cys Ser Thr Ser Ser
705                 710                 715                 720

Leu Leu Glu Ala Cys Thr Pro Arg Arg Pro
            725                 730

<210> SEQ ID NO 24
<211> LENGTH: 2196
<212> TYPE: DNA
<213> ORGANISM: Artificial Sequence
<220> FEATURE:
<223> OTHER INFORMATION: Heloderma suspectum homo sapien

<400> SEQUENCE: 24
catggtgaag gtactttac ttctgatttg tctaaacaaa tggaagaaga agctgttaga       60
ttgtttattg aatggttgaa aaatggtggt ccatcttctg gtgctccacc accatctcca     120
gaagctccaa ctgatccaga agctccaact gatgtaccta taaaactgt gagatggtgt     180 gcagtgtcgg agcatgaggc cactaagtgc cagagtttcc gcgaccatat gaaaagcgtc     240
attccatccg atggtcccag tgttgcttgt gtgaagaaag cctcctacct tgattgcatc     300
agggccattg cggcaaacga agcggatgct gtgacactgg atgcaggttt ggtgtatgat     360
gcttacctgg ctcccaataa cctgaagcct gtggtggcag agttctatgg gtcaaaagag     420
gatccacaga ctttctatta tgctgttgct gtggtgaaga aggatagtgg cttccagatg     480

```
aaccagcttc gaggcaagaa gtcctgccac acgggtctag gcaggtccgc tgggtggaac    540
atccccatag gcttacttta ctgtgactta cctgagccac gtaaacctct tgagaaagca    600
gtggccaatt tcttctcggg cagctgtgcc ccttgtgcgg atgggacgga cttcccccag    660
ctgtgtcaac tgtgtccagg gtgtggctgc tccacccta accaatactt cggctactcg    720
ggagccttca gtgtctgaa ggatggtgct ggggatgtgg cctttgtcaa gcactcgact    780
atatttgaga acttggcaaa caaggctgac agggaccagt atgagctgct ttgcctggac    840
aacacccgga agccggtaga tgaatacaag gactgccact tggcccaggt cccttctcat    900
accgtcgtgg cccgaagtat gggcggcaag gaggacttga tctgggagct tctcaaccag    960
gcccaggaac atttttggcaa agacaaatca aaagaattcc aactattcag ctctcctcat   1020
gggaaggacc tgctgtttaa ggactctgcc acgggttttt aaaagtccc ccccaggatg    1080
gatgccaaga tgtacctggg ctatgagtat gtcactgcca tccggaatct acgggaaggc   1140
acatgcccag aagccccaac agatgaatgc aagcctgtga gtggtgtgc gctgagccac   1200
cacgagaggc tcaagtgtga tgagtggagt gttaacagtg tagggaaaat agagtgtgta   1260
tcagcagaga ccaccgaaga ctgcatcgcc aagatcatga tggagaagc tgatgccatg   1320
agcttggatg gagggtttgt ctacatagcg ggcaagtgtg gtctggtgcc tgtcttggca   1380
gaaaactaca ataaggctga taattgtgag gatacaccag aggcagggta ttttgctgta   1440
gcagtggtga agaaatcagc ttctgacctc acctgggaca atctgaaagg caagaagtcc   1500
tgccatacgg cagttggcag aaccgctggc tggaacatcc ccatgggcct gctctacaat   1560
aagatcaacc actgcagatt tgatgaattt ttcagtgaag gttgtgcccc tgggtctaag   1620
aaagactcca gtctctgtaa gctgtgtatg ggctcaggcc taaacctctg tgaacccaac   1680
aacaaagagg gatactacgg ctacacaggc gctttcaggt gtctggttga agggagat    1740
gtggcctttg tgaaacacca gactgtccca cagaacactg ggggaaaaaa ccctgatcca   1800
tgggctaaga atctgaatga aaaagactat gagttgctgt gccttgatgg tactaggaaa   1860
cctgtggagg gtatgcgaa ctgccacctg gccagagccc cgaatcacgc tgtggtcaca   1920
cggaaagata aggaagcatg cgtccacaag atattacgtc aacagcagca cctatttgga   1980
agcaacgtag ctgactgctc gggcaacttt tgtttgttcc ggtcggaaac caaggacctt   2040
ctgttcagag atgacacagt atgtttggcc aaacttcatg acagaaacac atatgaaaaa   2100
tacttaggag aagaatatgt caaggctgtt ggtaacctga aaaatgctc cacctcatca   2160
ctcctggaag cctgcacttt ccgtcgacct taataa                             2196
```

<210> SEQ ID NO 25
<211> LENGTH: 749
<212> TYPE: PRT
<213> ORGANISM: Artificial Sequence
<220> FEATURE:
<223> OTHER INFORMATION: Heloderma suspectum homo sapien

<400> SEQUENCE: 25

```
Met Arg Leu Ala Val Gly Ala Leu Leu Val Cys Ala Val Leu Gly Leu
1               5                   10                  15

Cys Leu Ala His Gly Glu Gly Thr Phe Thr Ser Asp Leu Ser Lys Gln
            20                  25                  30

Met Glu Glu Glu Ala Val Arg Leu Phe Ile Glu Trp Leu Lys Asn Gly
        35                  40                  45

Gly Pro Ser Ser Gly Ala Pro Pro Ser Pro Glu Ala Pro Thr Asp
    50                  55                  60
```

-continued

Pro Glu Ala Pro Thr Asp Val Pro Asp Lys Thr Val Arg Trp Cys Ala
65                  70                  75                  80

Val Ser Glu His Glu Ala Thr Lys Cys Gln Ser Phe Arg Asp His Met
                85                  90                  95

Lys Ser Val Ile Pro Ser Asp Gly Pro Ser Val Ala Cys Val Lys Lys
            100                 105                 110

Ala Ser Tyr Leu Asp Cys Ile Arg Ala Ile Ala Ala Asn Glu Ala Asp
        115                 120                 125

Ala Val Thr Leu Asp Ala Gly Leu Val Tyr Asp Ala Tyr Leu Ala Pro
    130                 135                 140

Asn Asn Leu Lys Pro Val Val Ala Glu Phe Tyr Gly Ser Lys Glu Asp
145                 150                 155                 160

Pro Gln Thr Phe Tyr Tyr Ala Val Ala Val Lys Lys Asp Ser Gly
                165                 170                 175

Phe Gln Met Asn Gln Leu Arg Gly Lys Lys Ser Cys His Thr Gly Leu
            180                 185                 190

Gly Arg Ser Ala Gly Trp Asn Ile Pro Ile Gly Leu Leu Tyr Cys Asp
        195                 200                 205

Leu Pro Glu Pro Arg Lys Pro Leu Glu Lys Ala Val Ala Asn Phe Phe
    210                 215                 220

Ser Gly Ser Cys Ala Pro Cys Ala Asp Gly Thr Asp Phe Pro Gln Leu
225                 230                 235                 240

Cys Gln Leu Cys Pro Gly Cys Gly Cys Ser Thr Leu Asn Gln Tyr Phe
                245                 250                 255

Gly Tyr Ser Gly Ala Phe Lys Cys Leu Lys Asp Gly Ala Gly Asp Val
            260                 265                 270

Ala Phe Val Lys His Ser Thr Ile Phe Glu Asn Leu Ala Asn Lys Ala
        275                 280                 285

Asp Arg Asp Gln Tyr Glu Leu Leu Cys Leu Asp Asn Thr Arg Leu Pro
    290                 295                 300

Val Asp Glu Tyr Lys Asp Cys His Leu Ala Gln Val Pro Ser His Thr
305                 310                 315                 320

Val Val Ala Arg Ser Met Gly Gly Lys Glu Asp Leu Ile Trp Glu Leu
                325                 330                 335

Leu Asn Gln Ala Gln Glu His Phe Gly Lys Asp Lys Ser Lys Glu Phe
            340                 345                 350

Gln Leu Phe Ser Ser Pro His Gly Lys Asp Leu Leu Phe Lys Asp Ser
        355                 360                 365

Ala His Gly Phe Leu Lys Val Pro Pro Arg Met Asp Ala Lys Met Tyr
    370                 375                 380

Leu Gly Tyr Glu Tyr Val Thr Ala Ile Arg Asn Leu Arg Glu Gly Thr
385                 390                 395                 400

Cys Pro Glu Ala Pro Thr Asp Glu Cys Lys Pro Val Lys Trp Cys Ala
                405                 410                 415

Leu Ser His His Glu Arg Leu Lys Cys Asp Glu Trp Ser Val Asn Ser
            420                 425                 430

Val Gly Lys Ile Glu Cys Val Ser Ala Glu Thr Thr Glu Asp Cys Ile
        435                 440                 445

Ala Lys Ile Met Asn Gly Glu Ala Asp Ala Met Ser Leu Asp Gly Gly
    450                 455                 460

Phe Val Tyr Ile Ala Gly Lys Cys Gly Leu Val Pro Val Leu Ala Glu
465                 470                 475                 480

Asn Tyr Asn Lys Ala Asp Asn Cys Glu Asp Thr Pro Glu Ala Gly Tyr

```
                    485                 490                 495
Phe Ala Val Ala Val Lys Lys Ser Ala Ser Asp Leu Thr Trp Asp
            500                 505                 510
Asn Leu Lys Gly Lys Lys Ser Cys His Thr Ala Val Gly Arg Thr Ala
            515                 520                 525
Gly Trp Asn Ile Pro Met Gly Leu Leu Tyr Asn Lys Ile Asn His Cys
            530                 535                 540
Arg Phe Asp Glu Phe Phe Ser Glu Gly Cys Ala Pro Gly Ser Lys Lys
545                 550                 555                 560
Asp Ser Ser Leu Cys Lys Leu Cys Met Gly Ser Gly Leu Asn Leu Cys
            565                 570                 575
Glu Pro Asn Asn Lys Glu Gly Tyr Tyr Gly Tyr Thr Gly Ala Phe Arg
            580                 585                 590
Cys Leu Val Glu Lys Gly Asp Val Ala Phe Val Lys His Gln Thr Val
            595                 600                 605
Pro Gln Asn Thr Gly Gly Lys Asn Pro Asp Pro Trp Ala Lys Asn Leu
            610                 615                 620
Asn Glu Lys Asp Tyr Glu Leu Leu Cys Leu Asp Gly Thr Arg Lys Pro
625                 630                 635                 640
Val Glu Glu Tyr Ala Asn Cys His Leu Ala Arg Ala Pro Asn His Ala
            645                 650                 655
Val Val Thr Arg Lys Asp Lys Glu Ala Cys Val His Lys Ile Leu Arg
            660                 665                 670
Gln Gln Gln His Leu Phe Gly Ser Asn Val Ala Asp Cys Ser Gly Asn
            675                 680                 685
Phe Cys Leu Phe Arg Ser Glu Thr Lys Asp Leu Leu Phe Arg Asp Asp
            690                 695                 700
Thr Val Cys Leu Ala Lys Leu His Asp Arg Asn Thr Tyr Glu Lys Tyr
705                 710                 715                 720
Leu Gly Glu Glu Tyr Val Lys Ala Val Gly Asn Leu Arg Lys Cys Ser
            725                 730                 735
Thr Ser Ser Leu Leu Glu Ala Cys Thr Phe Arg Arg Pro
            740                 745

<210> SEQ ID NO 26
<211> LENGTH: 2253
<212> TYPE: DNA
<213> ORGANISM: Artificial Sequence
<220> FEATURE:
<223> OTHER INFORMATION: Heloderma suspectum Homo sapien

<400> SEQUENCE: 26
atgaggctcg ccgtgggagc cctgctggtc tgcgccgtcc tggggctgtg tctggcgcat      60
ggtgaaggta cttttacttc tgatttgtct aaacaaatgg aagaagaagc tgttagattg     120
tttattgaat ggttgaaaaa tggtggtcca tcttctggtg ctccaccacc atctccagaa     180
gctccaactg atccagaagc tccaactgat gtacctgata aaactgtgag atggtgtgca     240
gtgtcggagc atgaggccac taagtgccag agtttccgcg accatatgaa aagcgtcatt     300
ccatccgatg gtcccagtgt tgcttgtgtg aagaaagcct cctaccttga ttgcatcagg     360
gccattgcgg caaacgaagc ggatgctgtg acactggatg caggtttggt gtatgatgct     420
tacctggctc ccaataacct gaagcctgtg gtggcagagt tctatgggtc aaaagaggat     480
ccacagactt tctattatgc tgttgctgtg gtgaagaagg atagtggctt ccagatgaac     540
cagcttcgag gcaagaagtc ctgccacacg ggtctaggca ggtccgctgg gtggaacatc     600
```

```
cccataggct tactttactg tgacttacct gagccacgta aacctcttga gaaagcagtg    660
gccaatttct tctcgggcag ctgtgcccct tgtgcggatg ggacggactt cccccagctg    720
tgtcaactgt gtccagggtg tggctgctcc acccttaacc aatacttcgg ctactcggga    780
gccttcaagt gtctgaagga tggtgctggg gatgtggcct tgtcaagca ctcgactata    840
tttgagaact tggcaaacaa ggctgacagg gaccagtatg agctgctttg cctggacaac    900
acccggaagc cggtagatga atacaaggac tgccacttgg cccaggtccc ttctcatacc    960
gtcgtggccc gaagtatggg cggcaaggag gacttgatct gggagcttct caaccaggcc   1020
caggaacatt ttggcaaaga caaatcaaaa gaattccaac tattcagctc tcctcatggg   1080
aaggacctgc tgtttaagga ctctgcccac gggttttaa aagtcccccc caggatggat    1140
gccaagatgt acctgggcta tgagtatgtc actgccatcc ggaatctacg ggaaggcaca   1200
tgcccagaag ccccaacaga tgaatgcaag cctgtgaagt ggtgtgcgct gagccaccac   1260
gagaggctca gtgtgatga gtggagtgtt aacagtgtag ggaaaataga gtgtgtatca    1320
gcagagacca ccgaagactg catcgccaag atcatgaatg agaagctga tgccatgagc    1380
ttggatggag ggtttgtcta catagcgggc aagtgtggtc tggtgcctgt cttggcagaa   1440
aactacaata aggctgataa ttgtgaggat acaccagagg cagggtattt tgctgtagca   1500
gtggtgaaga aatcagcttc tgacctcacc tgggacaatc tgaaaggcaa gaagtcctgc   1560
catacggcag ttggcagaac cgctggctgg aacatcccca tgggcctgct ctacaataag   1620
atcaaccact gcagatttga tgaatttttc agtgaaggtt gtgcccctgg gtctaagaaa   1680
gactccagtc tctgtaagct gtgtatgggc tcaggcctaa acctctgtga acccaacaac   1740
aaagagggat actacggcta cacaggcgct tcaggtgtc tggttgagaa gggagatgtg    1800
gcctttgtga acaccagac tgtcccacag aacactgggg aaaaaaccc tgatccatgg    1860
gctaagaatc tgaatgaaaa agactatgag ttgctgtgcc ttgatggtac taggaaacct   1920
gtggaggagt atgcgaactg ccacctggcc agagccccga tcacgctgt ggtcacacgg    1980
aaagataagg aagcatgcgt ccacaagata ttacgtcaac agcagcacct atttggaagc   2040
aacgtagctg actgctcggg caacttttgt ttgttccggt cggaaaccaa ggaccttctg   2100
ttcagagatg acacagtatg tttggccaaa cttcatgaca gaaacacata tgaaaaatac   2160
ttaggagaag aatatgtcaa ggctgttggt aacctgagaa aatgctccac ctcatcactc   2220
ctggaagcct gcactttccg tcgaccttaa taa                                2253
```

<210> SEQ ID NO 27
<211> LENGTH: 12
<212> TYPE: PRT
<213> ORGANISM: Artificial Sequence
<220> FEATURE:
<223> OTHER INFORMATION: neutrophil lactoferrin splice variant

<400> SEQUENCE: 27

Glu Asp Cys Ile Ala Leu Lys Gly Glu Ala Asp Ala
1               5                   10

<210> SEQ ID NO 28
<211> LENGTH: 95
<212> TYPE: DNA
<213> ORGANISM: Artificial Sequence
<220> FEATURE:
<223> OTHER INFORMATION: PCR primer P0702

<400> SEQUENCE: 28
caataaacaa tctaacagct tcttcttcca tttgtttaga caaatcagaa gtaaaagtac    60
cttcaccatg cgccagacac agccccagga cggcg                           95

<210> SEQ ID NO 29
<211> LENGTH: 107
<212> TYPE: DNA
<213> ORGANISM: Artificial Sequence
<220> FEATURE:
<223> OTHER INFORMATION: PCR primer P0703

<400> SEQUENCE: 29
ggaagaagaa gctgttagat tgtttattga atggttgaaa aatggtggtc catcttctgg    60
tgctccacca ccatctgtac ctgataaaac tgtgagatgg tgtgcag               107

<210> SEQ ID NO 30
<211> LENGTH: 116
<212> TYPE: DNA
<213> ORGANISM: Heloderma suspectum

<400> SEQUENCE: 30
atggtgaagg tacttttact tctgatttgt ctaaacaaat ggaagaagaa gctgttagat    60
tgtttattga atggttgaaa aatggtggtc catcttctgg tgctccacca ccatct       116

<210> SEQ ID NO 31
<211> LENGTH: 18
<212> TYPE: DNA
<213> ORGANISM: Artificial Sequence
<220> FEATURE:
<223> OTHER INFORMATION: PCR primer P0177

<400> SEQUENCE: 31
gcgataaaga gcgcgatg                                                 18

<210> SEQ ID NO 32
<211> LENGTH: 20
<212> TYPE: DNA
<213> ORGANISM: Artificial Sequence
<220> FEATURE:
<223> OTHER INFORMATION: PCR primer P0014

<400> SEQUENCE: 32
ggctcaggta agtcacagta                                               20

<210> SEQ ID NO 33
<211> LENGTH: 47
<212> TYPE: DNA
<213> ORGANISM: Artificial Sequence
<220> FEATURE:
<223> OTHER INFORMATION: PCR primer P1810

<400> SEQUENCE: 33
ccaactgatc cagaagctcc aactgatgta cctgataaaa ctgtgag                 47

<210> SEQ ID NO 34
<211> LENGTH: 46
<212> TYPE: DNA
<213> ORGANISM: Artificial Sequence
<220> FEATURE:
<223> OTHER INFORMATION: PCR primer 1811

<400> SEQUENCE: 34
gcttctggat cagttggagc ttctggagat ggtggtggag caccag                  46

<210> SEQ ID NO 35
<211> LENGTH: 67

-continued

```
<212> TYPE: DNA
<213> ORGANISM: Artificial Sequence
<220> FEATURE:
<223> OTHER INFORMATION: PCR primer P0940

<400> SEQUENCE: 35
gtggtccacc agaagctcca actgatccag aagctccaac tgatgtacct gataaaactg    60
tgagatg                                                              67

<210> SEQ ID NO 36
<211> LENGTH: 43
<212> TYPE: DNA
<213> ORGANISM: Artificial Sequence
<220> FEATURE:
<223> OTHER INFORMATION: PCR primer P0941

<400> SEQUENCE: 36
tggagcttct ggtggaccac catttttcaa ccattcaata aac                      43

<210> SEQ ID NO 37
<211> LENGTH: 65
<212> TYPE: DNA
<213> ORGANISM: Artificial Sequence
<220> FEATURE:
<223> OTHER INFORMATION: PCR primer 0942

<400> SEQUENCE: 37
ggtggtccag aagctccaac tgatccagaa gctccaactg atgtacctga taaaactgtg    60
agatg                                                                65

<210> SEQ ID NO 38
<211> LENGTH: 35
<212> TYPE: DNA
<213> ORGANISM: Artificial Sequence
<220> FEATURE:
<223> OTHER INFORMATION: PCR primer 0943

<400> SEQUENCE: 38
gttggagctt ctggaccacc attttcaac cattc                                35

<210> SEQ ID NO 39
<211> LENGTH: 15
<212> TYPE: PRT
<213> ORGANISM: Artificial Sequence
<220> FEATURE:
<223> OTHER INFORMATION: Linker peptide

<400> SEQUENCE: 39

Gly Gly Gly Gly Ser Gly Gly Gly Gly Ser Gly Gly Gly Gly Ser
1               5                   10                  15

<210> SEQ ID NO 40
<211> LENGTH: 24
<212> TYPE: PRT
<213> ORGANISM: Homo sapiens

<400> SEQUENCE: 40

Met Lys Trp Val Ser Phe Ile Ser Leu Leu Phe Leu Phe Ser Ser Ala
1               5                   10                  15

Tyr Ser Arg Ser Leu Glu Lys Arg
            20

<210> SEQ ID NO 41
<211> LENGTH: 70
<212> TYPE: DNA
```

```
<213> ORGANISM: Homo sapiens

<400> SEQUENCE: 41
atgaagtggg ttagctttat ttcccttctt tttctcttta gctcggctta ttccaggagt    60
ctagagaaaa                                                           70

<210> SEQ ID NO 42
<211> LENGTH: 24
<212> TYPE: PRT
<213> ORGANISM: Homo sapiens

<400> SEQUENCE: 42

Met Lys Trp Val Phe Ile Val Ser Ile Leu Phe Leu Phe Ser Ser Ala
1               5                   10                  15

Tyr Ser Arg Ser Leu Glu Lys Arg
            20

<210> SEQ ID NO 43
<211> LENGTH: 72
<212> TYPE: DNA
<213> ORGANISM: Homo sapiens

<400> SEQUENCE: 43
atgaagtggg ttttcatcgt ctccattttg ttcttgttct cctctgctta ctctaggtct    60
ctagagaaaa gg                                                        72

<210> SEQ ID NO 44
<211> LENGTH: 6
<212> TYPE: PRT
<213> ORGANISM: Artificial Sequence
<220> FEATURE:
<223> OTHER INFORMATION: Pro-peptide sequence to ensure efficient
      removal of the signal sequence

<400> SEQUENCE: 44

Arg Ser Leu Asp Lys Arg
1               5

<210> SEQ ID NO 45
<211> LENGTH: 6
<212> TYPE: PRT
<213> ORGANISM: Artificial Sequence
<220> FEATURE:
<223> OTHER INFORMATION: Pro-peptide sequence to ensure efficient
      removal of the signal sequence

<400> SEQUENCE: 45

Arg Ser Leu Asp Arg Arg
1               5

<210> SEQ ID NO 46
<211> LENGTH: 6
<212> TYPE: PRT
<213> ORGANISM: Artificial Sequence
<220> FEATURE:
<223> OTHER INFORMATION: Pro-peptide sequence to ensure efficient
      removal of the signal sequence

<400> SEQUENCE: 46

Arg Ser Leu Glu Lys Arg
1               5

<210> SEQ ID NO 47
<211> LENGTH: 6
<212> TYPE: PRT
```

```
<213> ORGANISM: Artificial Sequence
<220> FEATURE:
<223> OTHER INFORMATION: Pro-peptide sequence to ensure efficient
      removal of the signal sequence

<400> SEQUENCE: 47

Arg Ser Leu Glu Arg Arg
1               5
```

FUSION PROTEIN OF AN EXENDIN TO MODIFIED TRANSFERRIN

CROSS-REFERENCE TO RELATED APPLICATIONS

This application is a divisional application of U.S. patent application Ser. No. 11/782,030, filed Jul. 24, 2007, now allowed, which is incorporated herein by reference, and which claims priority, under 35 U.S.C. §119(e), to U.S. Provisional Application Ser. Nos. 60/832,582, 60/857,474, and 60/874,965, filed on Jul. 24, 2006, Nov. 8, 2006, and Dec. 15, 2006, respectively, the entire disclosures of which are incorporated herein by reference.

FIELD OF THE INVENTION

The present invention relates to fusion proteins comprising an exendin-4 and a transferrin and uses thereof for the treatment of diseases associated with elevated glucose serum levels such as Type II diabetes, and to reduce body weight. The fusion protein of the invention can also be used to treat other diseases known to benefit from treatment with exendin-4 and other GLP-1 receptor agonists such as Type I diabetes, congestive heart failure, myocardial infarction, irritable bowel syndrome, neurological diseases such as Alzheimer's disease and Huntington's disease, and non-alcoholic, non-fatty liver disease.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. There are two generally recognized forms of diabetes. In Type diabetes, or insulin-dependent diabetes mellitus (IDDM), patients produce little or no insulin, the hormone which regulates glucose utilization. In Type II diabetes, or non-insulin dependent diabetes mellitus (NIDDM), patients often have plasma insulin levels that are the same or even elevated compared to nondiabetic subjects. However, these patients have developed a resistance to the insulin stimulating effect on glucose and lipid metabolism in the main insulin-sensitive tissues, which are muscle, liver and adipose tissues. The plasma insulin levels, while elevated, are insufficient to overcome the pronounced insulin resistance, resulting in hyperglycemia.

Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic diseases. For example, patients with Type II diabetes mellitus are at especially increased risk of macrovascular and microvascular complications, including coronary heart disease, stroke, peripheral vascular disease, hypertension, nephropathy, and neuropathy.

Obesity and being overweight are generally defined by body mass index (BMI), which is correlated with total body fat and serves as a measure of the risk of certain diseases. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or higher. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Overweight or obese individuals are at increased risk for ailments such as hypertension, dyslipidemia, Type II (non-insulin dependent) diabetes, insulin resistance, glucose intolerance, hyperinsulinemia, coronary heart disease, angina pectoris, congestive heart failure, stroke, gallstones, cholescystitis, cholelithiasis, gout, osteoarthritis, obstructive sleep apnea and respiratory problems, gall bladder disease, certain forms of cancer (e.g. endometrial, breast, prostate, and colon) and psychological disorders (such as depression, eating disorders, distorted body image and low self esteem). The negative health consequences of obesity make it the second leading cause of preventable death in the United States and impart a significant economic and psychosocial effect on society. See, McGinnis M, Foege W H., "Actual Causes of Death in the United States," *JAMA* 270:2207-12, 1993.

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5-10% loss of body weight can substantially improve metabolic values, such as blood glucose, blood pressure, and lipid concentrations. Hence, it is believed that a 5-10% reduction in body weight may reduce morbidity and mortality. Currently available prescription drugs for managing obesity generally reduce weight by decreasing dietary fat absorption, as with orlistat, or by creating an energy deficit by reducing food intake and/or increasing energy expenditure, as seen with sibutramine.

Current treatments for Type II diabetes include administration of exogenous insulin, oral administration of drugs and dietary therapies and exercise regimens. In 2005, exenatide (exendin-4; Byetta®) was FDA approved as an adjunct therapy for Type II diabetics who are taking metformin and/or a sulfonylurea but who have not achieved adequate glycemic control. Exenatide is exendin-4, a potent GLP-1 receptor agonist that is an endogenous product in the salivary glands of the Gila monster. Like GLP-1, exendin-4 is an incretin. It is insulinotropic, inhibits food intake and gastric emptying, and is trophic to β-cells in rodents (Parks et al., Metabolism. 50: 583-589, 2001; Aziz and Anderson, J. Nutr. 132: 990-995, 2002; and Egan et al., J. Clin. Endocrinol. Metab. 87: 1282-1290, 2002). Further, due to the presence of glycine at position 2 of its N-terminus, it is not a substrate for DPPIV, as is GLP-1. The downside to the use of exenatide is that it must be injected twice daily because its $t_{1/2}$ is only 2-4 hours (Kolterman et al., J. Clin. Endocrinol. Metab. 88: 3082-3089, 2003 and Fineman et al., Diabetes Care. 26: 2370-2377, 2003).

Accordingly, a need remains for a longer-fasting, degradation resistant GLP-1 receptor agonist molecule that can be used as a therapeutic to provide glycemic control and to reduce body weight. Development of a long acting incretin mimetic offers the ability to enhance glycemic control through continuous enhancement of glucose-dependent insulin secretion, with the convenience of less frequent dosing. The present invention fulfills this need by providing exendin-4 molecules fused to a modified transferrin, which extends the in vivo circulatory half-life of the exendin-4 while maintaining bioactivity. Additionally, use of a fusion protein of the invention may reduce the high incidence of nausea and vomiting currently associated with use of incretins.

SUMMARY OF THE INVENTION

The invention provides fusion proteins comprising an exendin-4 fused to a transferrin (Tf) molecule via a peptide linker, preferably, a nonhelical polypeptide linker.

Preferably, the linker is selected from the group consisting of PEAPTD (SEQ ID NO: 6), (PEAPTD)$_2$ (SEQ ID NO: 5), PEAPTD (SEQ ID NO: 6) in combination with an IgG hinge linker, and (PEAPTD)$_2$ (SEQ ID NO: 6) in combination with an IgG hinge linker. More preferably, the linker is (PEAPTD)$_2$ (SEQ ID NO: 5).

The Tf moiety of the fusion protein of the invention can originate from any mammalian Tf, preferably, from human Tf. More preferably, the Tf is modified (mTf) to exhibit reduced glycosylation as compared to a native transferrin molecule, and, even more preferably, the Tf has the amino acid sequence as shown in SEQ ID NO: 17. In other preferred embodiments, the Tf is modified to reduce iron binding and/or binding to the Tf receptor.

In another preferred embodiment, the N-terminus of the fusion protein further comprises a secretion signal sequence, preferably, a signal sequence from serum transferrin, lactoferrin, melanotransferrin, or a variant thereof, more preferably, a human serum albumin (HSA)/MFα-1 hybrid leader sequence, a modified HSA/MFα-1 hybrid leader sequence, or a Tf signal sequence, and, still more preferably, the signal sequence is the human Tf signal sequence (nL) as shown in SEQ ID NO: 18.

In a preferred embodiment, the invention provides a fusion protein comprising an exendin-4(1-39) (PEAPTD)$_2$ (SEQ ID NO: 5) mTf fusion protein, wherein said fusion protein comprises the amino acid sequence as shown in SEQ ID NO: 23 or SEQ ID NO: 25, the latter of which further comprises the nL leader sequence at the N-terminus. In other preferred embodiments, the exendin-4 is exendin-4(1-39) and has the amino acid sequence as shown in SEQ ID NO: 4, and/or the exendin-4 molecule is fused at the N-terminal end of the fusion protein, at the C-terminal end of the fusion protein or at both the N- and C-terminal ends of the fusion protein.

The invention also provides nucleic acid molecules encoding the above-described fusion proteins, as well as the corresponding vectors comprising the nucleic acid molecules, and host cells comprising the nucleic acid molecules and vectors.

Also featured by the invention is a pharmaceutical composition comprising any of the above-described fusion proteins and a pharmaceutically acceptable carrier.

In preferred embodiments, the pharmaceutical composition comprises the exendin-4(1-39) (PEAPTD)$_2$ (SEQ ID NO: 5) mTf fusion protein of SEQ ID NO: 23, and, in some embodiments, the composition comprising the exendin-4(1-39) (PEAPTD)$_2$ (SEQ ID NO: 5) mTf fusion protein of SEQ ID NO: 23 is adapted to be administered at a dose ranging from about 0.5 mg to about 50 mg or from about 1 mg to about 100 mg.

In another preferred embodiment, the composition is adapted to be administered via inhalation.

The invention also features a method of treating Type II diabetes or reducing blood glucose in a human patient in need thereof comprising administering to the patient a therapeutically effective amount of a fusion protein comprising an exendin-4 fused to a Tf via a polypeptide linker, preferably, a nonhelical linker.

Preferably, these methods comprise administering the exendin-4(1-39) (PEAPTD)$_2$ (SEQ ID NO: 5) mTf fusion protein comprising the amino acid sequence as shown in SEQ ID NO: 23, and, in certain embodiments, the fusion protein as shown in SEQ ID NO: 23 is administered at a dose of about 0.5 mg to about 50 mg at a frequency of about once per week, once per two weeks, or once per month. In another embodiment, the exendin-4 fused to a Tf via a polypeptide linker, preferably, a nonhelical linker, and, more preferably, the fusion protein as shown in SEQ ID NO: 23, is administered less frequently than exenatide to achieve therapeutic effectiveness at an equivalent therapeutic dose.

The invention also features a method of treating obesity or reducing body weight in a human patient in need thereof comprising administering a therapeutically effective amount of a fusion protein comprising an exendin-4 fused to a Tf via a polypeptide linker, preferably, a nonhelical linker. Preferably, the fusion protein comprises an exendin-4(1-39) (PEAPTD)$_2$ (SEQ ID NO: 5) mTf fusion protein comprising the amino acid sequence as shown in SEQ ID NO: 23, and, in certain embodiments, the fusion protein as shown in SEQ ID NO: 23 is administered at a dose of about 1 mg to about 100 mg at a frequency of about once per week, once per two weeks, or once per month. In another embodiment, the exendin-4 fused to a Tf via a polypeptide linker, preferably, the fusion protein as shown in SEQ ID NO: 23, is administered less frequently than exenatide to achieve therapeutic effectiveness.

The invention also provides for the use of an exendin-4/Tf fusion protein, or a pharmaceutical composition comprising the exendin/Tf fusion protein, preferably, an exendin-4(1-39) (PEAPTD)$_2$ (SEQ ID NO: 5) Tf fusion protein, and, more preferably, wherein the fusion protein is as shown in SEQ ID NO: 23, in the manufacture of a medicament for treating Type II diabetes or for reducing blood glucose in a patient in need thereof, preferably, wherein the medicament is adapted to be administered at a dose of about 0.5 mg to about 50 mg, or in the manufacture of a medicament for treating obesity or reducing body weight, in a human patient in need thereof, preferably, wherein the medicament is adapted to be administered at a dose of about 1 mg to about 100 mg.

By "exendin-4" is meant exendin-4 (1-39) as shown in SEQ ID NO: 4, as well as an exendin-4 fragment having with up to 8 or 9 amino acid residues removed from the C-terminal end of the sequence shown in SEQ ID NO: 4 to create, for example, an exendin-4(1-31) or exendin-4(1-30), as well as peptides having at least 90%, and, preferably, at least 95% identity to exendin-4(1-39), or one of the other above-described exendin-4 fragments.

As used herein, two or more DNA coding sequences are said to be "joined" or "fused" when, as a result of in-frame fusions between the DNA coding sequences, the DNA coding sequences are translated into a fusion polypeptide. The phrase "joined" or "fused" can also be used to refer to peptides fused by alternative methods, for instance, chemical methods. The term "fusion" in reference to transferrin (Tf) fusions includes, but is not limited to, attachment of at least one therapeutic protein, polypeptide or peptide to the N-terminal end of Tf, attachment to the C-terminal end of Tf, and/or insertion between any two amino acids within Tf.

By "pharmaceutically acceptable" is meant a substance or composition that must be compatible chemically and/or toxicologically with the other ingredients comprising a formulation, and/or the mammal being treated therewith.

By "therapeutically effective amount" means an amount of an exendin-4/Tf fusion protein of the present invention that reduces blood glucose, caloric intake, reduces body weight and/or reduces body fat with respect to appropriate control values determined prior to treatment or in a vehicle-treated group.

The terms "treating", "treat", or "treatment" embrace both preventative, i.e., prophylactic, and palliative treatment.

DETAILED DESCRIPTION OF THE INVENTION

Exendin-4/Tf Fusion Proteins

Figure 1B:
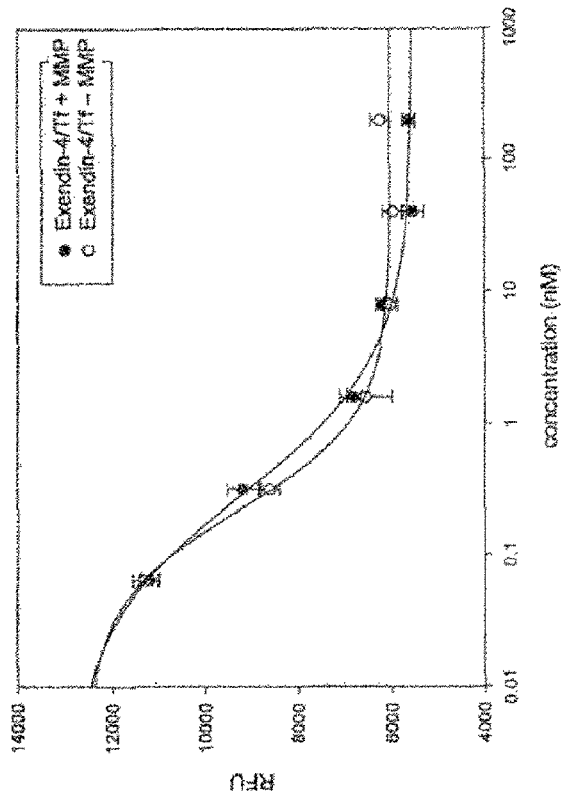
FIG. 1B is a graph showing collagenase resistance for the exendin-4(1-39) (PEAPTD)$_2$ (SEQ ID NO: 5) mTf fusion protein (exendin-4/Tf).

The exendin-4/Tf fusion protein of the present invention comprises exendin-4 fused to a Tf peptide via a polypeptide linker. Preferably, the full length exendin-4 (1-39) (SEQ ID NO.: 4) is used, or an exendin-4 fragment, with up to 8 or 9 amino acid residues removed from the C-terminal end of the sequence shown in SEQ ID NO: 4 to create, for example, an exendin-4 (1-31) or exendin-4(1-30).

Preferably, a non-helical polypeptide linker moiety is used to link the exendin-4 to the Tf.

The preferred linker is PEAPTDPEAPTD (SEQ ID NO: 5). Other linkers can be selected from the group consisting of PEAPTD (SEQ ID NO.: 6), PEAPTD (SEQ ID NO.: 6) in combination with an IgG hinge linker (SEQ ID NOS: 7-16), and PEAPTDPEAPTD (SEQ ID NO.: 5) in combination with an IgG hinge linker (SEQ ID NOS: 7-16). The fusion protein of the invention containing a substantially non-helical linker moiety may exhibit an increased productivity of expression as compared to a similar fusion protein without a substantially non-helical linker. Further, an exendin-4/Tf fusion protein containing a substantially non-helical linker may exhibit increased productivity of expression as compared to a similar fusion protein with a helical polypeptide linker.

The preferred exendin-4/Tf fusion protein comprises exendin-4(1-39) (SEQ ID NO: 4) linked, via linker (PEAPTD)$_2$ (SEQ ID NO: 5), to the mTf as provided in SEQ ID NO: 17. When produced, it is preferred that the exendin-4(1-39) (PEAPTD)$_2$ (SEQ ID NO: 5) mTf fusion protein also comprises the human transferrin secretion signal or leader sequence (nL) (SEQ ID NO: 18). The nucleic acid sequences encoding each of the components of the preferred exendin-4 (1-39) (PEAPTD)$_2$ (SEQ ID NO: 5) mTf fusion protein are as follows: nL leader sequence (SEQ ID NO: 19), exendin-4(1-39) (SEQ ID NO: 20), (PEAPTD)$_2$ (SEQ ID NO: 21), and the mTf (SEQ ID NO: 22). The amino acid sequence for the entire exendin-4(1-39) (PEAPTD)$_2$ (SEQ ID NO: 5) mTf fusion protein, without the nL leader is SEQ ID NO: 23; its corresponding nucleic acid sequence is SEQ ID NO: 24. The amino acid sequence of the entire exendin-4(1-39) (PEAPTD)$_2$ (SEQ ID NO: 5) mTf fusion protein with the nL leader sequence at the N-terminus is SEQ ID NO: 25; its corresponding nucleic acid sequence is SEQ ID NO: 26).

While the preferred mTf is described above, any transferrin may be used to make the exendin-4/Tf fusion proteins of the invention. As an example, the wild-type human Tf is a 679 amino acid protein of approximately 75 kDa (not accounting for glycosylation), with two main domains or lobes, N (about 330 amino acids) and C (about 340 amino acids), which appear to originate from a gene duplication. See GenBank accession numbers NM_001063, XM_002793, M12530, XM_039845, XM_039847 and S95936, all of which are herein incorporated by reference in their entirety, as well as SEQ ID NOS: 2 and 3 (SEQ ID NO: 2 comprises the additional 19 amino acid sequence of the nL human transferrin leader sequence). The two domains have diverged over time but retain a large degree of identity/similarity.

Each of the N and C lobes is further divided into two subdomains, N1 and N2, C1 and C2. The function of Tf is to transport iron to the cells of the body. This process is mediated by the Tf receptor (TfR), which is expressed on all cells, particularly actively growing cells. TfR recognizes the iron bound form of Tf (two molecules of which are bound per receptor), causing endocytosis whereby the TfR/Tf complex is transported to the endosome. The localized drop in pH in the endosome results in the release of bound iron and the recycling of the TfR/Tf complex to the cell surface and the release of Tf (known as apoTf in its iron-unbound form). Receptor binding occurs via the C domain of Tf. The two glycosylation sites in the C domain do not appear to be involved in receptor binding because iron bound Tf that is not glycosylated does bind the receptor.

Each Tf molecule can carry two iron ions ($Fe^{3+}$). These are complexed in the space between the N1 and N2, C1 and C2 sub domains resulting in a conformational change in the molecule.

For human transferrin of SEQ ID NO: 3, the iron binding sites comprise at least amino acids Asp 63 (Asp 82 of SEQ ID NO: 2 which includes the native Tf signal sequence), Asp 392 (Asp 411 of SEQ ID NO: 2), Tyr 95 (Tyr 114 of SEQ ID NO: 2), Tyr 426 (Tyr 445 of SEQ ID NO: 2), Tyr 188 (Tyr 207 of SEQ ID NO: 2), Tyr 514 or 517 (Tyr 533 or Tyr 536 SEQ ID NO: 2), His 249 (His 268 of SEQ ID NO: 2), and His 585 (His 604 of SEQ ID NO: 2). The hinge regions comprise at least N domain amino acid residues 94-96, 245-247 and/or 316-318 as well as C domain amino acid residues 425-427, 581-582 and/or 652-658 of SEQ ID NO: 3. The carbonate binding sites of the human Tf of SEQ ID NO: 3 comprise at least amino acids Thr 120 (Thr 139 of SEQ ID NO: 2), Thr 452 (Thr 471 of SEQ ID NO: 2), Arg 124 (Arg 143 of SEQ ID NO: 2), Arg 456 (Arg 475 of SEQ ID NO: 2), Ala 126 (Ala 145 of SEQ ID NO: 2), Ala 458 (Ala 477 of SEQ ID NO: 2), Gly 127 (Gly 146 of SEQ ID NO: 2), and Gly 459 (Gly 478 of SEQ ID NO: 2).

Preferably, the modified exendin-4/Tf fusion protein is of human origin, although any animal Tf molecule may be used to produce the fusion proteins of the invention, including human Tf variants, cow, pig, sheep, dog, rabbit, rat, mouse, hamster, echnida, platypus, chicken, frog, hornworm, monkey, as well as other bovine, canine and avian species. All of these Tf sequences are readily available in GenBank and other public databases. The human Tf nucleic acid sequence is available (see SEQ ID NO: 1 and the accession numbers described above) and can be used to make genetic fusions between Tf or a domain of Tf and the therapeutic molecule of choice. Fusions may also be made from related molecules such as lacto transferrin (lactoferrin) GenBank Acc: NM_002343) or murine melanotransferrin (GenBank Acc. NM_013900).

Melanotransferrin is a glycosylated protein found at high levels in malignant melanoma cells and was originally named human melanoma antigen p97 (Brown et al. 1982, Nature, 296: 171-173). It possesses high sequence homology with human serum transferrin, human lactoferrin, and chicken transferrin (Brown et al., Nature, 296: 171-173, 1982; Rose of al., Proc. Natl. Acad. Sci. USA, 83: 1261-1265, 1986). However, unlike these receptors, no cellular receptor has been identified for melanotransferrin. Melanotransferrin reversibly binds iron and it exists in two forms, one of which is bound to cell membranes by a glycosyl phosphatidylinositol anchor while the other form is both soluble and actively secreted (Baker et al., FEBS Lett, 298, 1992: 215-218; Alemany et al., J. Cell Sci., 104: 1155-1162, 1993; Food et al., J. Biol. Chem. 274: 7011-7017, 1994).

Lactoferrin (Lf), a natural defense iron-binding protein, has been found to possess antibacterial, antimycotic, antiviral, antineoplastic and anti-inflammatory activity. The protein is present in exocrine secretions that are commonly exposed to normal flora: milk, tears, nasal exudate, saliva, bronchial mucus, gastrointestinal fluids, cervico-vaginal mucus and seminal fluid. Additionally, Lf is a major constituent of the secondary specific granules of circulating polymorphonuclear neutrophils (PMNs). The apoprotein is released on degranulation of the PMNs in septic areas. A principal function of Lf is that of scavenging free iron in fluids and inflamed areas so as to suppress free radical-mediated damage and decrease the availability of the metal to invading microbial and neoplastic cells. In a study that examined the turnover rate of $^{125}$I Lf in adults, it was shown that Lf is rapidly taken up by the liver and spleen, and the radioactivity persisted for several weeks in the liver and spleen (Bennett et al., Clin. Sci. (Lond.) 57: 453-460, 1979).

The transferrin portion of the exendin-4/Tf fusion protein of the invention includes a transferrin splice variant. In one example, a transferrin splice variant can be a splice variant of human transferrin. Specifically, the human transferrin splice variant can be that of Genbank Accession AAA61140.

The transferrin portion of the exendin-4/Tf fusion protein of the invention includes a lactoferrin splice variant. In one example, a human serum lactoferrin splice variant can be a novel splice variant of a neutrophil lactoferrin. Specifically, the neutrophil lactoferrin splice variant can be that of the sequence displayed in Genbank Accession AAA59479. Also, the neutrophil lactoferrin splice variant can comprise the following amino acid sequence EDCIALKGEADA (SEQ ID NO: 27), which includes the novel region of splice-variance.

Alternatively, the transferrin portion of the exendin-4/Tf fusion protein of the invention includes a melanotransferrin variant.

Modified Tf fusions may be made with any Tf protein, fragment, domain, or engineered domain. For instance, fusion proteins may be produced using the full-length Tf sequence, with or without the native Tf signal sequence. Tf fusion proteins may also be made using a single Tf domain, such as an individual N or C domain or a modified form of Tf comprising 2N or 2C domains (see U.S. Pat. Appl. Publ. No. US 2006/0130158). Fusions of a therapeutic protein to a single C domain may be produced, wherein the C domain is altered to reduce inhibit or prevent glycosylation. Alternatively, the use of a single N domain is advantageous as the Tf glycosylation sites reside in the C domain and the N domain. Preferably, the Tf fusion protein has a single N domain which is expressed at a high level.

As used herein, a C terminal domain or lobe modified to function as an N-like domain is modified to exhibit glycosylation patterns or iron binding properties substantially like that of a native or wild-type N domain or lobe. Preferably, the C domain or lobe is modified so that it is not glycosylated and does not bind iron by substitution of the relevant C domain regions or amino acids to those present in the corresponding regions or sites of a native or wild-type N domain.

As used herein, a Tf moiety comprising "two N domains or lobes" includes a Tf molecule that is modified to replace the native C domain or lobe with a native or wild-type N domain or lobe or a modified N domain or lobe or contains a C domain that has been modified to function substantially like a wild-type or modified N domain.

Analysis of the two domains by overlay of the two domains (Swiss PDB Viewer 3.7b2, Iterative Magic Fit) and by direct amino acid alignment (ClustalW multiple alignment) reveals that the two domains have diverged over time. Amino acid alignment shows 42% identity and 59% similarity between the two domains. However, approximately 80% of the N domain matches the C domain for structural equivalence. The C domain also has several extra disulfide bonds compared to the N domain.

In one embodiment, the transferrin portion of the exendin-4/Tf fusion protein includes at least two N terminal lobes of transferrin. In further embodiments, the transferrin portion of the exendin-4/Tf fusion protein includes at least two N terminal lobes of transferrin derived from human serum transferrin.

The transferrin portion of the exendin-4/Tf fusion protein can also include: at least two N terminal lobes of transferrin having a mutation in at least one amino acid residue selected from the group consisting of Asp63, Gly65, Tyr95, Tyr188, and His249 of SEQ ID NO: 3; a recombinant human serum transferrin N-terminal lobe mutant having a mutation at Lys206 or His207 of SEQ ID NO: 3; or at least two C terminal lobes of transferrin. In further embodiments, the transferrin portion of the exendin-4/Tf fusion protein includes at least two C terminal lobes of transferrin derived from human serum transferrin.

In a further embodiment, the C terminal lobe mutant further includes a mutation of at least one of Asn413 and Asn611 of SEQ ID NO: 3 which does not allow glycosylation.

In another embodiment, the transferrin portion of the exendin-4/Tf fusion protein includes at least two C terminal lobes of transferrin having a mutation in at least one amino acid residue selected from the group consisting of Asp392, Tyr426, Tyr514, Tyr517 and His585 of SEQ ID NO: 3, wherein the mutant retains the ability to bind metal. In an alternate embodiment, the transferrin portion of the exendin-4/Tf fusion protein includes at least two C terminal lobes of transferrin having a mutation in at least one amino acid residue selected from the group consisting of Tyr426, Tyr514, Tyr517 and His585 of SEQ ID NO: 3, wherein the mutant has a reduced ability to bind metal. In another embodiment, the transferrin portion of the exendin-4/Tf fusion protein includes at least two C terminal lobes of transferrin having a mutation in at least one amino acid residue selected from the group consisting of Asp392, Tyr426, Tyr517 and His585 of SEQ ID NO:3, wherein the mutant does not retain the ability to bind metal and functions substantially like an N domain.

When the C domain of Tf is part of the fusion protein, the two N-linked glycosylation sites, amino acid residues corresponding to N413 and N611 of SEQ ID NO: 3 may be mutated for expression in a yeast system to prevent glycosylation or hypermannosylationn and extend the serum half-life of the fusion protein and/or therapeutic protein (to produce asialo-, or in some instances, monosialo-Tf or disialo-Tf). In addition to Tf amino acids corresponding to N413 and N611, mutations may be to the adjacent residues within the N-X-S/T glycosylation site to prevent or substantially reduce glycosylation. See U.S. Pat. No. 5,986,067. It has also been reported that the N domain of Tf expressed in *Pichia pastoris* becomes O-linked glycosylated with a single hexose at S32 which also may be mutated or modified to prevent such glycosylation.

Accordingly, the exendin-4/Tf fusion protein can also include a modified transferrin molecule wherein the transferrin exhibits reduced glycosylation, including but not limited to asialo-, monosialo- and disialo-forms of Tf. In another embodiment, the transferrin portion of the exendin-4/Tf fusion protein includes a recombinant transferrin mutant that is mutated to prevent glycosylation. The transferrin portion of the exendin-4/Tf fusion protein can also include a recombinant transferrin mutant that is fully glycosylated. In a further embodiment, the transferrin portion of the exendin-4/Tf fusion protein includes a recombinant human serum transferrin mutant that is mutated to prevent N-linked glycosylation, wherein at least one of Asn413 and Asn611 of SEQ ID NO: 3 is mutated to an amino acid which does not allow glycosylation. In another embodiment, the transferrin portion of the exendin-4/Tf fusion protein includes a recombinant human serum transferrin mutant that is mutated to prevent or substantially reduce glycosylation, wherein, for example, mutations are made to the adjacent residues within the N-X-S/T glycosylation site, for instance mutation of the S/T residues. Moreover, glycosylation may be reduced or prevented by mutating the serine or threonine residue. Further, changing the X to proline is known to inhibit glycosylation.

As discussed below in more detail, modified Tf fusion proteins of the invention may also be engineered to not bind iron and/or bind the Tf receptor. In other embodiments of the invention, the iron binding is retained and the iron binding ability of Tf may be used to deliver a therapeutic protein or peptide(s) to the inside of a cell, across an epithelial or endothelial cell membrane. These embodiments that bind iron and/or the Tf receptor will often be engineered to reduce or prevent glycosylation to extend the serum half-life of the therapeutic protein. The N domain alone will not bind to TfR when loaded with iron, and the iron bound C domain will bind TfR but not with the same affinity as the whole molecule.

Alternatively, the transferrin portion of the exendin-4/Tf fusion protein can include a recombinant transferrin mutant having a mutation wherein the mutant does not retain the ability to bind metal ions. In an alternate embodiment, the transferrin portion of the exendin-4/Tf fusion protein includes a recombinant transferrin mutant having a mutation wherein the mutant has a weaker binding affinity for metal ions than wild-type serum transferrin. In an alternate embodiment, the transferrin portion of the exendin-4/Tf fusion protein includes a recombinant transferrin mutant having a mutation wherein the mutant has a stronger binding affinity for metal ions than wild-type serum transferrin.

In another embodiment, the transferrin portion of the exendin-4/Tf fusion protein includes a recombinant transferrin mutant having a mutation wherein the mutant does not retain the ability to bind to the transferrin receptor. For instance, the exendin-4 and Tf fusion proteins of the invention may bind a cell surface GLP-1 receptor but not a Tf receptor. Such fusion proteins can be therapeutically active at the cell surface, i.e., without entering the cell.

Alternatively, the transferrin portion of the exendin-4/Tf fusion protein can include: a recombinant transferrin mutant having a mutation wherein the mutant has a weaker binding affinity for the transferrin receptor than wild-type serum transferrin; a recombinant transferrin mutant having a mutation wherein the mutant has a stronger binding affinity for the transferrin receptor than wild-type serum transferrin; a recombinant transferrin mutant having a mutation wherein the mutant does not retain the ability to bind to carbonate ions; a recombinant transferrin mutant having a mutation wherein the mutant has a weaker binding affinity for carbonate ions than wild-type serum transferrin; or a recombinant transferrin mutant having a mutation wherein the mutant has a stronger binding affinity for carbonate ions than wild-type serum transferrin.

In another embodiment, the transferrin portion of the exendin-4/Tf fusion protein includes a recombinant human serum transferrin mutant having a mutation in at least one amino acid residue selected from the group consisting of Asp63, Gly65, Tyr95, Tyr188, His249, Asp392, Tyr426, Tyr514, Tyr517 and His585 of SEQ ID NO: 3, wherein the mutant retains the ability to bind metal ions. In an alternate embodiment, a recombinant human serum transferrin mutant has a mutation in at least one amino acid residue selected from the group consisting of Asp63, Gly65, Tyr95, Tyr188, His249, Asp392, Tyr426, Tyr514, Tyr517 and His585 of SEQ ID NO: 3, wherein the mutant has a reduced ability to bind metal ions. In another embodiment, a recombinant human serum transferrin mutant having a mutation in at least one amino acid residue selected from the group consisting of Asp63, Gly65, Tyr95, Tyr188, His249, Asp392, Tyr426, Tyr517 and His585 of SEQ ID NO: 3, wherein the mutant does not retain the ability to bind metal ions.

In another embodiment, the transferrin portion of the exendin-4/Tf fusion protein includes a recombinant human serum transferrin mutant having a mutation at Lys206 or His207 of SEQ ID NO:3, wherein the mutant has a stronger binding affinity for metal ions than wild-type human serum transferrin (see U.S. Pat. No. 5,986,067). In an alternate embodiment, the transferrin portion of the exendin-4/Tf fusion protein includes a recombinant human serum transferrin mutant having a mutation at Lys206 or His207 of SEQ ID NO:3, wherein the mutant has a weaker binding affinity for metal ions than wild-type human serum transferrin. In a further embodiment, the transferrin portion of the exendin-4/Tf fusion protein includes a recombinant human serum transferrin mutant having a mutation at Lys206 or His207 of SEQ ID NO:3, wherein the mutant does not bind metal ions.

Any available technique may be used to produce the exendin-4/Tf fusion proteins of the invention, including but not limited to molecular techniques commonly available, for instance, those disclosed in Sambrook et al. Molecular Cloning: A Laboratory Manual, 2nd Ed., Cold Spring Harbor Laboratory Press, 1989. When carrying out nucleotide substitutions using techniques for accomplishing site-specific mutagenesis that are well known in the art, the encoded amino acid changes are preferably of a minor nature, that is, conservative amino acid substitutions, although other, non-conservative, substitutions are contemplated as well, particularly when producing a modified transferrin portion of a Tf fusion protein, e.g., a modified Tf protein exhibiting reduced glycosylation, reduced iron binding and the like. Specifically contemplated are amino acid substitutions, small deletions or insertions, typically of one to about 30 amino acids; insertions between transferrin domains; small amino- or carboxyl-terminal extensions, such as an amino-terminal methionine residue, or small linker peptides of less than 50, 40, 30, 20 or 10 residues between transferrin domains or linking a transferrin protein and an exendin-4 or a small extension that facilitates purification, such as a poly-histidine tract, an antigenic epitope or a binding domain.

Examples of conservative amino acid substitutions are substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

Non-conservative substitutions encompass substitutions of amino acids in one group by amino acids in another group. For example, a non-conservative substitution would include the substitution of a polar amino acid for a hydrophobic amino acid. For a general description of nucleotide substitution, see e.g. Ford et al., Prot. Exp. Pur. 2: 95-107, 1991. Non-conservative substitutions, deletions and insertions are particularly useful to produce Tf fusion proteins of the invention that exhibit no or reduced binding of iron, no or reduced binding of the fusion protein to the Tf receptor and/or no or reduced glycosylation.

Iron binding and/or receptor binding may be reduced or disrupted by mutation, including deletion, substitution or insertion into, amino acid residues corresponding to one or more of Tf N domain residues Asp63, Tyr95, Tyr188, His249 and/or C domain residues Asp 392, Tyr 426, Tyr 514 and/or His 585 of SEQ ID NO: 3. Iron binding may also be affected by mutation to amino acids Lys206, His207 or Arg632 of SEQ ID NO: 3. Carbonate binding may be reduced or disrupted by mutation, including deletion, substitution or insertion into, amino acid residues corresponding to one or more of Tf N domain residues Thr120, Arg124. Ala126, Gly 127 and/or C domain residues Thr 452, Arg 456, Ala 458 and/or Gly 459 of SEQ ID NO: 3. A reduction or disruption of carbonate binding may adversely affect iron and/or receptor binding.

Binding to the Tf receptor may be reduced or disrupted by mutation, including deletion, substitution or insertion into, amino acid residues corresponding to one or more of Tf N domain residues described above for iron binding.

As discussed above, glycosylation may be reduced or prevented by mutation, including deletion, substitution or insertion into, amino acid residues corresponding to one or more of Tf C domain residues around the N-X-S/T sites corresponding to C domain residues N413 and/or N611 (See U.S. Pat. No. 5,986,067). For instance, the N413 and/or N611 may be mutated to Glu residues.

In instances where the Tf fusion proteins of the invention are not modified to prevent glycosylation, iron binding, carbonate binding and/or receptor binding, glycosylation, iron and/or carbonate ions may be stripped from or cleaved off of the fusion protein. For instance, available deglycosylases may be used to cleave glycosylation residues from the fusion protein, in particular the sugar residues attached to the Tf portion, yeast deficient in glycosylation enzymes may be used to prevent glycosylation and/or recombinant cells may be grown in the presence of an agent that prevents glycosylation, e.g., tunicamycin.

The carbohydrates on the fusion protein may also be reduced or completely removed enzymatically by treating the fusion protein with deglycosylases. Deglycosylases are well known in the art. Examples of deglycosylases include but are not limited to galactosidase, PNGase A, PNGase F, glucosidase, mannosidase, fucosidase, and Endo H deglycosylase.

Nevertheless, in certain circumstances, it may be preferable for oral delivery that the Tf portion of the fusion protein be fully glycosylated.

Additional mutations may be made with Tf to alter the three dimensional structure of Tf, such as modifications to the hinge region to prevent the conformational change needed for iron binding and Tf receptor recognition. For instance, mutations may be made in or around N domain amino acid residues 94-96, 245-247 and/or 316-318 as well as C domain amino acid residues 425-427, 581-582 and/or 652-658. In addition, mutations may be made in or around the flanking regions of these sites to alter Tf structure and function.

The exendin-4/Tf fusion protein can function as a carrier protein to extend the half life or bioavailability of the therapeutic protein as well as, in some instances, delivering the therapeutic protein inside a cell and/or across the blood-brain barrier (BBB). In an alternate embodiment, the fusion protein includes a modified transferrin molecule wherein the transferrin does not retain the ability to cross the BBB.

In another embodiment, the exendin-4/Tf fusion protein includes a modified transferrin molecule wherein the transferrin molecule retains the ability to bind to the transferrin receptor and transport the therapeutic peptide inside cells. In an alternate embodiment, the exendin-4/Tf fusion protein includes a modified transferrin molecule wherein the transferrin molecule does not retain the ability to bind to the transferrin receptor and transport the therapeutic peptide inside cells.

In further embodiments, the exendin-4/Tf fusion protein includes a modified transferrin molecule wherein the transferrin molecule retains the ability to bind to the transferrin receptor and transport the therapeutic peptide inside cells and retains the ability to cross the BBB. In an alternate embodiment, the exendin-4/Tf fusion protein includes a modified transferrin molecule wherein the transferrin molecule retains the ability to cross the BBB, but does not retain the ability to bind to the transferrin receptor and transport the therapeutic peptide inside cells.

The modified fusion proteins of the present invention can be composed of amino acids joined to each other by peptide bonds or modified peptide bonds and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature.

Modifications can occur anywhere in a polypeptide, including the peptide backbone, the amino acid side-chains and the amino or carboxy termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, glycosylation, GPI anchor formation, hydroxylation, iodination, methylation, myristylation, oxidation, pegylation, proteolytic processing, phosphorylation, prenylation, racemization, sulfation, transfer-RNA mediated addition of amino acids to proteins such as arginylation, and ubiquitination. (See, e.g., Proteins—Structure and Molecular Properties, 2nd Ed., T. E. Creighton, W. H. Freeman and Company, New York, 1993; Post-translational Covalent Modification of Proteins, B. C. Johnson, Ed., Academic Press, New York, pgs. 1-12, 1983; and Seifter et al. Meth. Enzymol. 182:626-646, 1990).

Nucleic Acid Molecules Encoding Exendin-4/Tf

The present invention also provides nucleic acid molecules encoding the exendin-4/Tf fusion proteins. A preferred nucleic acid molecule encodes SEQ ID NO: 23, which is the amino acid sequence of exendin-4(1-39), linked by (PEAPTD)$_2$ (SEQ ID NO: 5), to an mTf. An exemplary nucleic acid sequence is shown as SEQ ID NO: 24. Most preferably, the nucleic acid sequence of the present invention encodes SEQ ID NO: 25, which is the amino acid sequence of exendin-4(1-39) (PEAPTD)$_2$ (SEQ ID NO: 5) mTf fusion protein plus an additional N-terminal 19 amino acids representing the human transferrin secretion signal or leader sequence. An exemplary nucleic acid sequence encoding SEQ ID NO: 25 is shown as SEQ ID NO: 26.

Sequences that encode an exendin-4/Tf fusion protein can also include a stop codon (e.g., tga, taa, tag) at the C-terminal end, and can readily be obtained in a variety of ways including, without limitation, chemical synthesis, genetic mutation of wild type exendin-4 and transferrin polynucleotide sequences obtained from cDNA or genomic library screening, expression library screening, and/or polymerase chain reaction (PCR) amplification of cDNA. Nucleic acid molecules encoding an exendin-4/Tf fusion protein may be produced using site directed mutagenesis, PCR amplification, or other appropriate methods, where the primer(s) have the desired point mutations. Recombinant DNA methods and mutagenesis methods described herein are generally those set forth in Sambrook et al., Molecular Cloning: A Laboratory Manual, Cold Spring Harbor Laboratory Press, 1989, and Current Protocols in Molecular Biology, Ausubel at al., Green Publishers Inc. and Wiley and Sons, 1994.

Nucleic acid polynucleotides encoding the amino acid sequence an exendin-4/Tf fusion protein may be identified by expression cloning which employs the detection of positive clones based upon a property of the expressed protein. Typically, nucleic acid libraries are screened by the binding of an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce exendin-4/Tf fusion protein encoding polynucleotides and to express the encoded polypeptides. For example, by inserting a nucleic acid sequence that encodes the amino acid sequence of an exendin-4/Tf fusion protein into an appropriate vector, one skilled in the art can readily produce large quantities of the desired nucleotide sequence. The sequences can then be used to generate detection probes or amplification primers. Alternatively, a polynucleotide encoding the amino acid sequence of an exendin-4/Tf fusion protein can be inserted into an expression vector. By introducing the expression vector into an appropriate host, the encoded exendin-4/Tf fusion protein may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA encoding the amino acid sequence of an exendin-4/Tf fusion protein, are then added to the cDNA along with a polymerase such as Taq polymerase, and the polymerase amplifies the cDNA region between the two primers.

The DNA fragment encoding the amino-terminus of the polypeptide can have an ATG, which encodes a methionine residue. This methionine may or may not be present on the mature form of the exendin-4/Tf fusion protein, depending on whether the polypeptide produced in the host cell is designed to be secreted from that cell. The codon encoding isoleucine can also be used as a start site. Other methods known to the skilled artisan may be used as well. In certain embodiments, nucleic acid variants contain codons which have been altered for optimal expression of an exendin-4/Tf fusion protein in a given host cell. Particular codon alterations will depend upon the exendin-4/Tf fusion protein and the host cell selected for expression. Such codon optimization can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "*Drosophila*_high.cod," "Human_high.cod," "Maize_high.cod," and "Yeast_high.cod."

Vectors

A nucleic acid molecule encoding the amino acid sequence of an exendin-4/Tf fusion protein is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of an exendin-4/Tf fusion protein may be amplified/expressed in prokaryotic, yeast, insect (baculovirus systems) and/or eukaryotic host cells. For a review of expression vectors, see Meth. Enz., vol. 185, D. V. Goeddel, Academic Press, 1990.

Typically, expression vectors used in any of the host cells will contain sequences for plasmid maintenance and for cloning and expression of exogenous nucleotide sequences. Such sequences, collectively referred to as "flanking sequences" in certain embodiments, will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of an exendin-4/Tf fusion protein coding sequence; the oligonucleotide sequence encodes polyHis (such as hexa-His), or another "tag" such as FLAG, HA (hemaglutinin influenza virus), or myc for which commercially available antibodies exist. This tag is typically fused to the polypeptide upon expression of the polypeptide, and can serve as a means for affinity purification of the exendin-4/Tf fusion protein from the host cell. Affinity purification can be accomplished, for example, by column chromatography using antibodies against the tag as an affinity matrix. Optionally, the tag can subsequently be removed from the purified exendin-4/Tf fusion protein by various means such as using certain peptidases for cleavage, e.g., enterokinase digestion 3' of a FLAG tag sequence that is upstream of the one of the amino acid sequences.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate exendin-4 expression. The source of a flanking sequence may be any prokaryotic or eukaryotic organism, any vertebrate or invertebrate organism, or any plant, provided that the flanking sequence is functional in, and can be activated by, the host cell machinery.

Useful flanking sequences may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Qiagen, Chatsworth, Calif.), or other methods known to the skilled artisan. The selection of suitable enzymes to accomplish this purpose will be readily apparent to one of skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of an exendin-4/Tf fusion protein. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes an exendin-4/Tf fusion protein. As a result, increased quantities of an exendin-4/Tf fusion protein are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the exendin-4/Tf fusion protein to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

The terms "secretory signal sequence" or "signal sequence" or "secretion leader sequence" are used interchangeably and are described, for example, in U.S. Pat. Nos. 6,291,212 and 5,547,871. Secretory signal sequences or signal sequences or secretion leader sequences encode secretory peptides. A secretory peptide is an amino acid sequence that acts to direct the secretion of a mature polypeptide or protein from a cell. Secretory peptides are generally characterized by a core of hydrophobic amino acids and are typically (but not exclusively) found at the amino termini of newly synthesized proteins. Very often the secretory peptide is cleaved from the mature protein during secretion. Secretory peptides may contain processing sites that allow cleavage of the signal peptide from the mature protein as it passes through the secretory pathway. Processing sites may be encoded within the signal peptide or may be added to the signal peptide by, for example, in vitro mutagenesis.

Secretory peptides may be used to direct the secretion of the fusion proteins of the invention. One such secretory peptide that may be used in combination with other secretory peptides is the alpha mating factor leader sequence. Secretory signal sequences or signal sequences or secretion leader sequences are required for a complex series of post-translational processing steps which result in secretion of a protein. If an intact signal sequence is present, the protein being expressed enters the lumen of the rough endoplasmic reticulum and is then transported through the Golgi apparatus to secretory vesicles and is finally transported out of the cell. Generally, the signal sequence immediately follows the initiation codon and encodes a signal peptide at the amino-terminal end of the protein to be secreted. In most cases, the signal sequence is cleaved off by a specific protease, called a signal peptidase. Preferred signal sequences improve the processing and export efficiency of recombinant protein expression using viral, mammalian or yeast expression vectors.

In one embodiment, the native Tf signal sequence may be used to express and secrete fusion proteins of the present invention. Since transferrin molecules exist in various types of secretions such as blood, tears, and milk, there are many different transferrin signal peptides. For example, the transferrin signal peptide could be from serum transferrin, lactotransferrin, or melanotransferrin. The native transferrin signal peptide also could be from various species such as insects, mammals, fish, frog, duck, chicken, or other species. Preferably, the signal peptide is from a mammalian transferrin molecule. More preferably, the signal peptide is from human serum transferrin. The signal peptide sequences from various mammalian transferrin molecules are described in U.S. Pat. Appl. Publ. No. 2006/0205037.

Preferably, the transferrin derived signal sequence may be used to secrete a heterologous protein, for instance, any protein of interest that is heterologous to the Tf signal sequence may be expressed and secreted using a Tf signal. In particular, a Tf signal sequence may be used to secrete proteins from recombinant yeast. Preferably, the signal peptide is from human serum transferrin (SEQ ID NO: 18; encoded by SEQ ID NO: 19). Other preferred signal peptides include HSA/MFα-1 (SEQ ID NO: 40; encoded by SEQ ID NO: 41), and modified HSA/MFα-1 (SEQ ID NO: 42; encoded by SEQ ID NO: 43).

In order to ensure efficient removal of the signal sequence, in some cases it may be preferable to include a short pro-peptide sequence between the signal sequence and the mature protein in which the C-terminal portion of the pro-peptide comprises a recognition site for a protease, such as the yeast kex2p protease. Preferably, the pre-peptide sequence is about 2-12 amino acids in length, more preferably about 4-8 amino acids in length. Examples of such pro-peptides are Arg-Ser-Leu-Asp-Lys-Arg (SEQ ID NO: 44), Arg-Ser-Leu-Asp-Arg-Arg (SEQ ID NO: 45), Arg-Ser-Leu-Glu-Lys-Arg (SEQ ID NO: 46), and Arg-Ser-Leu-Glu-Arg-Arg (SEQ ID NO: 47).

Expression and cloning vectors will typically contain a promoter that is recognized by the host organism and operably linked to the molecule encoding the exendin-4/Tf fusion protein. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding an exendin-4/Tf fusion protein by removing the promoter from the source DNA by restriction enzyme digestion and inserting the desired promoter sequence into the vector. The native exendin-4 or transferrin promoter sequence may be used to direct amplification and/or expression of an exendin-4/Tf fusion protein nucleic acid molecule. However, a heterologous promoter is preferred, if it permits greater transcription and higher yields of the expressed protein as compared to the native promoter, and if it is compatible with the host cell system that has been selected for use.

Suitable promoters for use with yeast hosts are also well known in the art and are further discussed below. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Promoters suitable for use with prokaryotic hosts include the beta-lactamase and lactose promoter systems; *E. coli* T7 inducible RNA polymerase; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Additional promoters which may be of interest in controlling expression of an exendin-4/Tf fusion protein include, but are not limited to: the SV40 early promoter region (Bemoist and Chambon, Nature 290:304-10, 1981); the CMV promoter; the promoter contained in the 3' long terminal repeat of Rous sarcoma virus (Yamamoto et al, Cell 22:787-97, 1980); the herpes thymidine kinase promoter (Wagner et al., Proc. Natl. Acad. Sci. 78:1444-45, 1981); the regulatory sequences of the metallothionine gene (Brinster et al., Nature 296:39-42, 1982); prokaryotic expression vectors such as the beta-lactamase promoter (Villa-Kamaroff et al., Proc. Natl. Acad. Sci. U.S.A. 75:3727-31, 1978); or the tac promoter (DeBoer et al., Proc. Natl. Acad. Sci. U.S.A., 80:21-25, 1983).

An enhancer sequence may be inserted into the vector to increase the transcription in higher eukaryotes of a DNA encoding an exendin-4/Tf fusion protein. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-fetoprotein, and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to an exendin-4/Tf fusion protein encoding nucleic acid molecule, it is typically located at a site 5' to the promoter.

Expression vectors may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Suitable yeast vectors for use in the present invention are described, for example, in U.S. Pat. No. 6,291,212 and include YRp7 (Struhl et al., Proc. Natl. Acad. Sci. USA 76: 1035-1039, 1978), YEp13 (Broach et al., Gene 8: 121-133, 1979), pJDB249 and pJDB219 (Beggs, Nature 275:104-108, 1978), pPPC0005, pSeCHSA, pScNHSA, pC4 and derivatives thereof. Useful yeast plasmid vectors also include pRS403-406, pRS413-416 and the *Pichia* vectors available from Stratagene Cloning Systems (La Jolla, Calif.). Plasmids pRS403, pRS404, pRS405 and pRS406 are Yeast integrating plasmids (YIps) and incorporate the yeast selectable markers HIS3, TRP1, LEU2 and URA3. PlasmidspRS413~41.6 are Yeast Centromere plasmids (YCps).

Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. supra), URA3 (Botstein et al., Gene 8: 17, 1979), HIS3 (Struhl et al., supra) or POT1 (Kawasaki and Bell, European Pat. No. EP 171,142). Other suitable selectable markers include the CAT gene, which confers chloramphenicol resistance on yeast cells. Preferred promoters for use in yeast include promoters from yeast glycolytic genes (Hitzeman et al., J. Biol. Chem. 225: 12073-12080, 1980; Alber and Kawasaki, J. Mol. Appl. Genet. 1: 419-434, 1982; Kawasaki, U.S. Pat. No. 4,599,311) or alcohol dehydrogenase genes (Young at al., in Genetic Engineering of Microorganisms for Chemicals, Hollaender et al., p. 355, Plenum, N.Y., 1982; Ammerer, Meth. Enzymol. 101: 192-201, 1983). In this regard, particularly preferred promoters are the TPI1 promoter (Kawasaki, U.S. Pat. No. 4,599,311) and the ADH2-4$^C$ (see U.S. Pat. No. 6,291,212 promoter (Russell et al., Nature 304: 652-654, 1983). The expression units may also include a transcriptional terminator. A preferred transcriptional terminator is the TPI1 terminator (Alber and Kawasaki, supra). Other preferred vectors and preferred components such as promoters and terminators of a yeast expression system are disclosed in European Pat. Nos. EP 0258067, EP 0286424, EP0317254, EP 0387319, EP 0386222, EP 0424117, EP 0431880, EP 1002095EP, EP 0828759, EP 0764209, EP 0749478, and EP 0889949; PCT Publ. Nos. WO 00/44772 and WO 94/04687; and U.S. Pat. Nos. 5,739,007, 5,637,504, 5,302,697, 5,260,202, 5,667,986, 5,728,553, 5,783,423, 5,965,386, 6,150,133, 6,379,924, and 5,714,377.

In addition to yeast, fusion proteins of the present invention can be expressed in filamentous fungi, for example, strains of the fungi *Aspergillus*. Examples of useful promoters include those derived from *Aspergillus nidulans* glycolytic genes, such as the adh3 promoter (McKnight et al., EMBO J. 4: 2093-2099, 1985) and the tpiA promoter. An example of a suitable terminator is the adh3 terminator (McKnight et al., supra). The expression units utilizing such components may be cloned into vectors that are capable of insertion into the chromosomal DNA of *Aspergillus*, for example.

Other vectors are those which are compatible with bacterial, insect, and mammalian host cells. Such vectors include, inter alia, pCRII, pCR3, and pcDNA3.1 (Invitrogen, Carlsbad, Calif.), pBSII (Stratagene), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Appl. Publ. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to, plasmids such as Bluescript® plasmid derivatives (a high copy number ColE1-based phagemid, Stratagene), RCA cloning plasmids designed for cloning Taq-amplified PCR products (e.g., TOPO® TA Cloning® Kit, PCR2.1® plasmid derivatives, Invitrogen), and mammalian, yeast or virus vectors such as a baculovirus expression system (pBacPAK plasmid derivatives, Clontech).

Also contained in the expression vectors is a polyadenylation signal located downstream of the coding sequence of interest. Polyadenylation signals include the early or late polyadenylation signals from SV40 (Kaufman and Sharp, supra), the polyadenylation signal from the adenovirus 5 E1B region and the human growth hormone gene terminator (DeNato at al., Nucl. Acid Res. 9: 3719-3730, 1981). A particularly preferred polyadenylation signal is the $V_H$ gene terminator (see U.S. Pat. No. 6,291,212). The expression vectors may include a noncoding viral leader sequence, such as the adenovirus 2 tripartite leader, located between the promoter and the RNA splice sites. Preferred vectors may also include enhancer sequences, such as the SV40 enhancer and the mouse (see U.S. Pat. No. 6,291,212) enhancer (Gillies, Cell 33: 717-728, 1983). Expression vectors may also include sequences encoding the adenovirus VA RNAs.

After the vector has been constructed and a nucleic acid molecule encoding an exendin-4/Tf fusion protein has been inserted into the proper site of the vector, the completed vector may be inserted into a suitable host cell for amplification and/or polypeptide expression. The transformation of an expression vector for an exendin-4/Tf fusion protein into a selected host cell may be accomplished by well known methods including methods such as transfection, infection, electroporation, microinjection, lipofection, DEAE-dextran method, or other known techniques. The method selected will, in part, be a function of the type of host cell to be used. These methods and other suitable methods are well known to the skilled artisan, and are set forth, for example, in Sambrook at al., Molecular Cloning: A Laboratory Manual, 2nd Ed., Cold Spring Harbor Laboratory Press, 1989. Cloned DNA sequences comprising fusion proteins of the invention may be introduced into cultured mammalian cells by, for example, calcium phosphate-mediated transfection (Wigler at al., Cell 14: 725, 1978; Corsaro and Pearson, Somatic Cell Genetics 7: 603, 1981; Graham and Van der Eb, Virology 52: 456, 1973.) Other techniques for introducing cloned DNA sequences into mammalian cells, such as electroporation (Neumann at al., EMBO J. 1: 841-845, 1982), or lipofection may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. A particularly preferred amplifiable marker is the DHFR' (see U.S. Pat. No. 6,291, 212) cDNA (Simonsen and Levinson, Proc. Natl. Acad. Sci. USA 80: 2495-2499, 1983). Selectable markers are reviewed by Thilly (Mammalian Cell Technology, Butterworth Publishers, Stoneham, Mass.) and the choice of selectable markers is well within the level of ordinary skill in the art.

Host Cells

The present invention also includes a cell, preferably, a yeast cell, transformed to express an exendin-4/Tf fusion protein of the invention. In addition to the transformed host cells themselves, the present invention also includes a culture of those cells, preferably a monoclonal (clonally homogeneous) culture, or a culture derived from a monoclonal culture, in a nutrient medium. If the polypeptide is secreted, the medium will contain the polypeptide, with the cells, or without the cells if they have been filtered or centrifuged away.

Particularly useful host cells to produce the exendin-4/Tf fusion proteins of the invention are the methylotrophic yeast *Pichia pastoris* (Steinlein at al., Protein Express. Purif. 6:619-624, 1995). *P. pastoris* has been developed to be an outstanding host for the production of foreign proteins since its alcohol oxidase promoter was isolated and cloned; its transformation was first reported in 1985. *P. pastoris* can utilize methanol as a carbon source in the absence of glucose. The *P. pastoris* expression system can use the methanol-induced alcohol oxidase (AOX1) promoter, which controls the gene that codes for the expression of alcohol oxidase, the enzyme which catalyzes the first step in the metabolism of methanol. This promoter has been characterized and incorporated into a series of *P. pastoris* expression vectors. Since the proteins produced in *P. pastoris* are typically folded correctly and secreted into the medium, the fermentation of genetically engineered *P. pastoris* provides an excellent alternative to *E. coli* expression systems. A number of proteins have been produced using this system, including tetanus toxin fragment, *Bordatella pertussis* pertactin, human serum albumin and lysozyme.

Strains of the yeast *Saccharomyces cerevisiae* are another preferred host. In a preferred embodiment, a yeast cell, or more specifically, a *S. cerevisiae* host cell that contains a genetic deficiency in a gene required for asparagine-linked glycosylation of glycoproteins is used. *S. cerevisiae* host cells having such defects may be prepared using standard techniques of mutation and selection, although many available yeast strains have been modified to prevent or reduce glycosylation or hypermannosylation. Ballou et al. (J. Biol. Chem. 255; 5986-5991, 1980) have described the isolation of mannoprotein biosynthesis mutants that are defective in genes which affect asparagine-linked glycosylation. Gentzsch and Tanner (Glycobiology 7:481-486, 1997) have described a family of at least six genes (PMT1-6) encoding enzymes responsible for the first step in O-glycosylation of proteins in yeast. Mutants defective in one or more of these genes show reduced O-linked glycosylation and/or altered specificity of O-glycosylation.

In one embodiment, the host is a *S. cerevisiae* strain described in PCT Pat. Appl. Publ. No. WO 05/061718. For instance, the host can contain a pSAC35 based plasmid carrying a copy of the PDI1 gene or any other chaperone gene in a strain with the host version of PDI1 or other chaperone knocked out, respectively. Such a construct confers enhanced stability.

To optimize production of the heterologous proteins, it is also preferred that the host strain carries a mutation, such as the *S. cerevisiae* pep4 mutation (Jones, Genetics 85: 23-33, 1977), which results in reduced proteolytic activity. Host strains containing mutations in other protease encoding regions are particularly useful to produce large quantities of the exendin-4/Tf fusion proteins of the invention.

The host cell, when cultured under appropriate conditions, synthesizes an exendin-4/Tf fusion protein which can subsequently be collected from the culture medium (it the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Other host cells may be prokaryotic host cells (such as *E. coli*) or eukaryotic host cells (such as insect or vertebrate cell). A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., Proc. Natl. Acad. Sci. U.S.A. 97:4216-20, 1980), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines are monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as suitable host cells are bacterial cells. For example, the various strains of *E. coli* (e.g., HB101, DH5α, DH10, and MC1061) are well known as host cells in the field of biotechnology. Various strains of *B. subtilis*, *Pseudomonas* spp., other *Bacillus* spp., and *Streptomyces* spp. may also be employed.

Additionally, where desired, insect cell systems may be utilized for the expression of an exendin-4/Tf fusion protein. Such systems are described, for example, in Kitts et al., Biotechniques 14:810-17, 1993; Lucklow, Curr. Opin. Biotechnol. 4:564-72, 1993; and Lucklow et al., J. Virol., 67:4566-79, 1993. Preferred insect cells are Sf-9 and Hi5 (Invitrogen).

Exendin-4/Tf Fusion Protein Production

Host cells containing DNA constructs of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct. Yeast cells, for example, are preferably grown in a chemically defined medium, comprising a carbon source, e.g. sucrose, a non-amino acid nitrogen source, inorganic salts, vitamins and essential amino acid supplements. The pH of the medium is preferably maintained at a pH greater than 2 and less than 8, preferably at pH 5.5-6.5. Methods for maintaining a stable pH include buffering and constant pH control. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1 M and 1.5 M, preferably at 0.5 M or 1.0 M.

Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum, as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

Baculovirus/insect cell expression systems may also be used to produce the modified Tf fusion proteins of the invention. The BacPAK™ Baculovirus Expression System (BD Biosciences (Clontech)) expresses recombinant proteins at high levels in insect host cells. The target gene is inserted into a transfer vector, which is cotransfected into insect host cells with the linearized BacPAK6 viral DNA. The BacPAK6 DNA is missing an essential portion of the baculovirus genome. When the DNA recombines with the vector, the essential element is restored and the target gene is transferred to the baculovirus genome. Following recombination, a few viral plaques are picked and purified, and the recombinant phenotype is verified. The newly isolated recombinant virus can then be amplified and used to infect insect cell cultures to produce large amounts of the desired protein.

The exendin-4/Tf fusion proteins of the present invention may also be produced using transgenic plants and animals. For example, sheep and goats can make the therapeutic protein in their milk. Or tobacco plants can include the protein in their leaves. Both transgenic plant and animal production of proteins comprises adding a new gene coding the fusion protein into the genome of the organism. Not only can the transgenic organism produce a new protein, but it can also pass this ability onto its offspring.

The amount of an exendin-4/Tf fusion protein produced by a host cell can be evaluated using standard methods known in the art. Such methods include, without limitation, Western blot analysis, SDS-polyacrylamide gel electrophoresis, nondenaturing gel electrophoresis, High Performance Liquid Chromatography (HPLC) separation, immunoprecipitation, and/or activity assays such as DNA binding gel shift assays.

If an exendin-4/Tf fusion protein has been designed to be secreted from the host cell line, the majority of polypeptide may be found in the cell culture medium. If, however, the polypeptide is not secreted from the host cells, it will be present in the cytoplasm and/or the nucleus (for eukaryotic host cells) or in the cytosol (for gram-negative bacteria host cells).

For an exendin-4/Tf fusion protein situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication, followed by centrifugation.

If an exendin-4/Tf fusion protein has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized exendin-4/Tf fusion protein can then be analyzed using gel electrophoresis, immunoprecipitation, or the like. If it is desired to isolate the polypeptide, isolation may be accomplished using standard methods such as those described herein and in Marston et al., Meth. Enz. 182:264-75, 1990.

If inclusion bodies are not formed to a significant degree upon expression of an exendin-4/Tf fusion protein, then the polypeptide will be found primarily in the supernatant after centrifugation of the cell homogenate. The polypeptide may be further isolated from the supernatant using methods such as those described herein.

A number of additional methods for producing polypeptides are known in the art, and the methods can be used to produce an exendin-4/Tf fusion protein. See, e.g., Roberts et al., Proc. Natl. Acad. Sci. U.S.A. 94:12297-303, 1997, which describes the production of fusion proteins between an mRNA and its encoded peptide. See also, Roberts, Curr. Opin. Chem. Biol. 3:268-73, 1999.

Processes for producing peptides or polypeptides are also described in U.S. Pat. Nos. 5,763,192, 5,814,476, 5,723,323, and 5,817,483. The process involves producing stochastic genes or fragments thereof, and then introducing these genes into host cells which produce one or more proteins encoded by the stochastic genes. The host cells are then screened to identify those clones producing peptides or polypeptides having the desired activity. Other processes for recombinant peptide expression are disclosed in U.S. Pat. Nos. 6,103,495, 6,210,925, 6,627,438, and 6,737,250. The process utilizes E. coli and the E. coli general secretory pathway. The peptide is fused to a signal sequence; thus, the peptide is targeted for secretion.

Another method for producing peptides or polypeptides is described in PCT Pat. Appl. Publ. No. WO 99/15650. The published process, termed random activation of gene expression for gene discovery, involves the activation of endogenous gene expression or over expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

Isolation/Purification of Exendin-4/Tf Fusion Proteins

Secreted, biologically active, exendin-4/Tf fusion proteins may be isolated from the medium of host cells grown under conditions that allow the secretion of the biologically active fusion proteins. The cell material is removed from the culture medium, and the biologically active fusion proteins are isolated using isolation techniques known in the art. Suitable isolation techniques include precipitation and fractionation by a variety of chromatographic methods, including gel filtration, ion exchange chromatography and affinity chromatography.

A particularly preferred purification method is affinity chromatography on an iron binding or metal chelating column or an immunoaffinity chromatography using an antigen directed against the transferrin or therapeutic protein of the polypeptide fusion. The antigen is preferably immobilized or attached to a solid support or substrate. In one embodiment, the substrate is CNBr-activated Sepharose (Pharmacia LKB Technologies, Inc., Piscataway, N.J.). By this method, the medium is combined with the antigen/substrate under conditions that will allow binding to occur. The complex may be washed to remove unbound material, and the exendin-4/Tf fusion protein is released or eluted through the use of conditions unfavorable to complex formation. Particularly useful methods of elution include changes in pH, wherein the immobilized antigen has a high affinity for the exendin-4/Tf fusion protein at a first pH and a reduced affinity at a second (higher or lower) pH; changes in concentration of certain chaotropic agents; or through the use of detergents.

The purification of an exendin-4/Tf fusion protein from solution can be accomplished using a variety of techniques. If the polypeptide has been synthesized such that it contains a tag such as Hexahistidine 9 or other small peptide such as FLAG (Eastman Kodak Co., New Haven, Conn.) or myc (Invitrogen) at either its carboxyl or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification. See, Current Protocols in Molecular Biology, §10.11.8 (supra).

Additionally, an exendin-4/Tf fusion protein may be purified through the use of a monoclonal antibody that is capable of specifically recognizing and binding to an exendin-4/Tf fusion protein.

When it is preferable to partially or completely purify an exendin-4/Tf fusion protein such that it is partially or substantially free of contaminants, standard methods known to those skilled in the art may be used. Such methods include, without limitation, separation by electrophoresis followed by electroelution, various types of chromatography (affinity, immunoaffinity, molecular sieve, and ion exchange), HPLC, and preparative isoelectric focusing ("Isoprime" machine/technique, Hoefer Scientific, San Francisco, Calif.). In some cases, two or more purification techniques may be combined to achieve increased purity.

Pharmaceutical Compositions

The exendin-4/Tf fusion proteins of the present invention will generally be administered in the form of a pharmaceutical composition. The pharmaceutical composition may, for example, be in a form suitable for oral administration (e.g., a tablet, capsule, pill, powder, solution, suspension), for parenteral injection (e.g., a sterile solution, suspension or emulsion), for intranasal administration (e.g., an aerosol drops, etc), for rectal administration (e.g., a suppository) or for transdermal (e.g., a patch). The pharmaceutical composition may be in unit dosage forms suitable for single administration of precise dosages. The pharmaceutical composition will include an exendin-4/Tf fusion protein of the invention as an active ingredient and can include a conventional pharmaceutical carrier. In addition, it may include other pharmaceutical agents, adjuvants, etc.

Methods of preparing various pharmaceutical compositions of bioactive peptides are known in the pharmaceutical sciences art. For example, see U.S. Pat. Appl. Publ. No. 2005/0009748 (for oral administration); and U.S. Pat. Appl. Publ. Nos. 2004/0157777, 2005/0002927 and 2005/0215475 (for transmucosal administration, e.g., intranasal or buccal administration). See also Remington: The Practice of Pharmacy, Lippincott Williams and Wilkins, Baltimore, Md., 20$^{th}$ ed., 2000.

Traditionally, peptide and protein drugs have been administered by injection because of the poor bioavailability when administered orally. These drugs are prone to chemical and conformational instability and are often degraded by the acidic conditions in the stomach, as well as by enzymes in the stomach and gastrointestinal tract. In response to these delivery problems, certain technologies for oral delivery have been developed, such as encapsulation in nanoparticles composed of polymers with a hydrophobic backbone and hydrophilic branches as drug carriers, encapsulation in microparticles, insertion into liposomes in emulsions, and conjugation to other molecules. All of which may be used with the fusion molecules of the present invention.

Examples of nanoparticles include mucoadhesive nanoparticles coated with chitosan and Carbopol (Takeuchi et al., Adv. Drug Deliv. Rev. 47: 39-54, 2001) and nanoparticles containing charged combination polyesters, poly(2-sulfobutyl-vinyl alcohol) and poly(D,L-lactic-co-glycolic acid) (Jung et al., Eur. J. Pharm. Biopharm. 50: 147-160, 2000). Nanoparticles containing surface polymers with poly-N-isopropylacrylamide regions and cationic poly-vinylamine groups showed improved absorption of salmon calcitonin when administered orally to rats.

Drug delivery particles composed of alginate and pectin, strengthened with polylysine, are relatively acid and base resistant and can be used as a carrier for drugs. These particles combine the advantages of bioadhesion, enhanced absorption and sustained release (Liu et al., J. Pharm. Pharmacol. 51: 141-149, 1999).

Additionally, lipoamino acid groups and liposaccharide groups conjugated to the N- and C-termini of peptides such as synthetic somatostatin, creating an amphipathic surfactant, were shown to produce a composition that retained biological activity (Toth et al., J. Med. Chem. 42(19):4010-4013, 1999).

Examples of other peptide delivery technologies include carbopol-coated mucoadhesive emulsions containing the peptide of interest and either nitroso-N-acetyl-D,L-penicillamine and carbolpol or taurocholate and carbopol. These were shown to be effective when orally administered to rats to reduce serum calcium concentrations (Ogiso et al., Biol. Pharm. Bull, 24: 656-661, 2001). Phosphatidylethanol, derived from phosphatidylcholine, was used to prepare liposomes containing phosphatidylethanol as a carrier of insulin. These liposomes, when administered orally to rats, were shown to be active (Kisel et al., Int. J. Pharm. 216: 105-114, 2001).

Insulin has also been formulated in polyvinyl alcohol)-gel spheres containing insulin and a protease inhibitor, such as aprotinin or bacitracin. The glucose-lowering properties of these gel spheres have been demonstrated in rats, where insulin is released largely in the lower intestine (Kimura et al., Biol. Pharm. Bull. 19: 897-900, 1996.

Oral delivery of insulin has also been studied using nanoparticles made of poly(alkyl cyanoacrylate) that were dispersed with a surfactant in an oily phase (Damge et al., J. Pharm. Sci. 86: 1403-1409, 1997) and using calcium alginate beads coated with chitosan (Onal et al., Artif. Cells Blood Substit. Immobil. Biotechnol. 30: 229-237, 2002).

In other methods, the N- and C-termini of a peptide are linked to polyethylene glycol and then to allyl chains to form conjugates with improved resistance to enzymatic degradation and improved diffusion through the GI wall (www.nobexcorp.com).

BioPORTER® is a cationic lipid mixture, which interacts non-covalently with peptides to create a protective coating or layer. The peptide-lipid complex can fuse to the plasma membrane of cells, and the peptides are internalized into the cells.

In a process using liposomes as a starting material, cochleate-shaped particles have been developed as a pharmaceutical vehicle. A peptide is added to a suspension of liposomes containing mainly negatively charged lipids. The addition of calcium causes the collapse and fusion of the liposomes into large sheets composed of lipid bilayers, which then spontaneously roll up or stack into cochleates (U.S. Pat. No. 5,840,707).

Moreover, the present invention includes pulmonary delivery of the exendin-4/Tf fusion protein formulations. Pulmonary delivery is particularly promising for the delivery of macromolecules which are difficult to deliver by other routes of administration. Such pulmonary delivery can be effective both for systemic delivery and for localized delivery to treat diseases of the lungs, since drugs delivered to the lung are readily absorbed through the alveolar region directly into the blood circulation.

The present invention provides compositions suitable for forming a drug dispersion for oral inhalation (pulmonary delivery) to treat various conditions or diseases. The fusion protein formulation could be delivered by different approaches such as liquid nebulizers, aerosol-based metered dose inhalers (MRI's), and dry powder dispersion devices. In formulating compositions for pulmonary delivery, pharmaceutically acceptable carriers including surface active agents or surfactants and bulk carriers are commonly added to provide stability, dispersibility, consistency, and/or bulking characteristics to enhance uniform pulmonary delivery of the composition to the subject.

Surface active agents or surfactants promote absorption of polypeptide through mucosal membrane or lining. Useful surface active agents or surfactants include fatty acids and salts thereof, bile salts, phospholipid, or an alkyl saccharide. Examples of fatty acids and salts thereof include sodium, potassium and lysine salts of caprylate ($C_8$), caprate ($C_{10}$), laurate ($C_{12}$) and myristate ($C_{14}$). Examples of bile salts include cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid.

Examples of phospholipids include single-chain phospholipids, such as lysophosphatidylcholine, lysophosphatidylglycerol, lysophosphatidylethanolamine, lysophosphatidylinositol and lysophosphatidylserine, or double-chain phospholipids, such as diacylphosphatidylcholines, diacylphosphatidylglycerols, diacylphosphatidylethanolamines, diacylphosphatidylinositols and diacylphosphatidylserines. Examples of alkyl saccharides include alkyl glucosides or alkyl maltosides, such as decyl glucoside and dodecyl maltoside.

Pharmaceutical excipients that are useful as carriers include stabilizers such as human serum albumin (HSA), bulking agents such as carbohydrates, amino acids and polypeptides; pH adjusters or buffers, and salts such as sodium chloride. These carriers may be in a crystalline or amorphous form or may be a mixture of the two.

Examples of carbohydrates for use as bulking agents include monosaccharides such as galactose, D-mannose, and sorbose, disaccharides, such as lactose and trehalose; cyclodextrins, such as 2-hydroxypropyl-.beta.-cyclodextrin, and polysaccharides, such as raffinose, maltodextrins, and extrans, alditols, such as mannitol and xylitol. Examples of polypeptides for use as bulking agents include aspartame. Amino acids include alanine and glycine, with glycine being preferred.

Additives, which are minor components of the composition, may be included for conformational stability during spray drying and for improving dispersibility of the powder. These additives include hydrophobic amino acids such as tryptophan, tyrosine, leucine, and phenylalanine.

Suitable pH adjusters or buffers include organic salts prepared from organic acids and bases, such as sodium citrate, and sodium ascorbate; sodium citrate is preferred.

The GLP-1 receptor agonist fusion compositions for pulmonary delivery may be packaged as unit doses where a therapeutically effective amount of the composition is present in a unit dose receptacle, such as a blister pack or gelatin capsule. The manufacture of blister packs or gelatin capsules is typically carried out by methods that are generally well known in the packaging art.

U.S. Pat. No. 6,524,557 discloses a pharmaceutical aerosol formulation comprising (a) a HFA propellant (b) a pharmaceutically active polypeptide dispersible in the propellant; and (c) a surfactant which is a $C_8$-$C_{16}$ fatty acid or salt thereof, a bile salt, a phospholipid, or an alkyl saccharide, which surfactant enhances the systemic absorption of the polypeptide in the lower respiratory tract. The invention also provides methods of manufacturing such formulations and the use of such formulations in treating patients.

One approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation.

Dry powder dispersion devices are described in several patents, U.S. Pat. No. 3,921,637 describes a manual pump with needles for piercing through a single capsule of powdered medicine. The use of multiple receptacle disks or strips of medication is described in European Pat. No. EP 0 467 172; PCT Pat. Appl. Publ. Nos. WO 91/02558 and WO 93/09832; and U.S. Pat. Nos. 4,627,432, 4,811,731, 5,035,237, 5,048,514, 4,446,862, 5,048,514, and 4,446,862.

The aerosolization of protein therapeutic agents is disclosed in European Pat. No. EP 0 289 336. Therapeutic aerosol formulations are disclosed in PCT Pat. Appl. Publ. No. WO 90/09781.

Methods of Treatment

The exendin-4/Tf fusion proteins of this invention may be used in conjunction with other pharmaceutical agents for the treatment of the disease states or conditions described herein. Therefore methods of treatment that include administering compounds of the present invention in combination with other pharmaceutical agents are also provided by the present invention.

In the methods aspect of the invention, an exendin-4/Tf fusion protein of the invention, alone or in combination with one or more other pharmaceutical agents, is peripherally administered to a subject separately or together in any of the conventional methods of peripheral administration known in the art. Accordingly, the exendin-4/Tf fusion protein or combination may be administered to a subject parenterally (e.g., intravenously, intraperitoneally, intramuscularly or subcutaneously), intranasally, orally, sublingually, buccally, by inhalation (e.g., by aerosol), rectally (e.g., by suppositories) or transdermally. Parenteral, but non-oral, administration (e.g., injection) is a preferred method of administration, and subcutaneous administration is a preferred method of parenteral administration. Pulmonary delivery by inhalation is also a preferred method of administration.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate.

These compositions for parenteral injection may also contain excipients such as preserving, wetting, solubilizing, emulsifying, and dispersing agents. Prevention of microorganism contamination of the compositions can be accomplished with various antibacterial and antifungal agents, for example, parabens, chlorobutanol, phenol, and sorbic acid. It may also be desirable to include isotonic agents, for example, sugars and sodium chloride. Prolonged absorption of injectable pharmaceutical compositions can be brought about by the use of agents capable of delaying absorption, for example, aluminum monostearate and gelatin.

The exendin-4/Tf fusion proteins of the present invention will be administered to a subject at a dosage that varies depending on a number of factors, including the mode of administration, the age and weight of the subject, the severity of the disease, condition or disorder being treated, and the pharmacological activity of the exendin-4/Tf fusion protein being administered. The determination of dosage ranges and optimal dosages for a particular patient is well within the ordinary skill in the art.

For parenteral injection for treatment to reduce blood glucose, the exendin-4(1-39) (PEAPTD)$_2$ (SEQ ID NO: 5) mTf fusion protein as shown in SEQ ID NO: 23 may be administered to a human subject at dosage levels in the range of about 0.5-50 mg per dose, more preferably, 0.5-20 mg per dose, with dose administration occurring about once per week, once per two weeks, or once per month.

For parenteral injection for treatment to reduce body weight, the dose range may be higher than that for reducing blood glucose. Therefore, for parenteral administration for treatment to reduce body weight, the exendin-4(1-39) (PEAPTD)$_2$ (SEQ ID NO: 5) mTf fusion protein as shown in SEQ ID NO: 23 may be administered to a human subject at dosage levels in the range of about 1-100 mg per dose, with dose administration occurring about once per week, once per two weeks, or once per month.

The invention also provides an exendin-4/Tf fusion protein of the invention for use in treating Type II diabetes or reducing blood glucose in a human patient. Further provided is an exendin-4/Tf fusion protein of the invention for use in treating obesity or decreasing food intake in a human patient. A further aspect of the invention provides the use of an exendin-4/Tf fusion protein of the invention in the manufacture of a medicament for treating Type II diabetes or reducing blood glucose in a human patient. A yet further aspect provides the use of an exendin-4/Tf fusion protein of the invention in the manufacture of a medicament for treating obesity or decreasing food intake. Features of the methods aspect of the invention may apply to each of these aspects.

Embodiments of the present invention are illustrated by the following Examples. It is to be understood, however, that the embodiments of the invention are not limited to the specific details of these Examples, as other variations thereof will be known, or apparent in light of the instant disclosure and appendant claims, to one of ordinary skill in the art. All references cited herein are hereby incorporated by reference in their entireties.

EXAMPLES

Example 1

Construction of Exendin-4/Tf Fusion Proteins

Exendin-4(1-39) (PEAPTD)$_2$ (SEQ ID NO: 5) mTf Fusion Protein

The exendin-4(1-39) DNA sequence (SEQ ID NO: 20) was inserted between the secretion signal sequence (nL) (SEQ ID NO: 19) and mTf sequence (SEQ ID NO: 22) of pREX0549 using site overlapping extension (SOE) PCR. Two primers were designed, P0702 (SEQ ID NO: 28) and P0703 (SEQ ID NO: 29), to insert the sequence using pREX0549 as a template.

The DNA sequence was obtained by back translation of the exendin-4 amino acid sequence using codons optimal for yeast expression (SEQ ID NO: 30). Initially two PCR products were created using a primer 5' of the AflIII site, P0177 (SEQ ID NO: 31) with P0702, or a primer 3' of the BamHI site, P0014 (SEQ ID NO: 32) with P0703. The products from these reactions were gel purified and joined using only the outer primers, P0177 and P0014, in a second round of PCR.

The product from this second reaction was gel purified and digested with the restriction enzymes AflIII and BamHI, as was the plasmid pREX0549. The appropriate products from these reactions were ligated together to give pREX0561, which was DNA sequenced between the AflIII and BamHI sites to confirm correct insertion of the exendin-4 sequence. The expression cassette was recovered from pREX0561 by restriction enzyme digestion with NotI and ligated into NotI-digested, calf intestinal alkaline phosphatase-treated pSAC35 to give pREX0589.

Using pREX0561 as a template, SOE PCR was performed with the primers P1810 (SEQ ID NO: 33) and P1811 (SEQ ID NO: 34) to introduce the linker peptide sequence (PEAPTD)$_2$ (SEQ ID NO.: 21) between the encoded C-terminus of the exendin-4 sequence and the N-terminus of the encoded mTf sequence using the same procedure as described above.

The final product from this PCR was gel purified and digested with the restriction enzymes AflIII and BamHI, as was the plasmid pREX0549. The appropriate products from these reactions were ligated together to give pREX0935, which was DNA sequenced between the AflIII and BamHI sites to confirm correct insertion of the sequence encoding (PEAPTD)$_2$ (SEQ ID NO:5). The expression cassette was recovered from pREX0935 by restriction enzyme digestion with NotI and ligated into NotI-digested, alkaline phosphatase-treated pSAC35 to give pREX0936. The amino acid sequence for the exendin-4(1-39) (PEAPTD)$_2$ (SEQ ID NO: 5) mTf fusion protein, without the nL leader sequence, is provided herein as SEQ ID NO: 23. The nucleic acid sequence encoding SEQ ID NO: 23 is provided herein as SEQ ID NO: 24. The amino acid sequence for the exendin-4(1-39) (PEAPTD)$_2$ (SEQ ID NO: 5) mTf fusion protein with the nL leader sequence is provided herein as SEQ ID NO: 25. The nucleic acid sequence encoding SEQ ID NO: 25 is provided herein as SEQ ID NO: 26.

Additional Exendin-4/Tf Constructs

Exendin-4 has an additional 9 amino acids at the C-terminus as compared to GLP-1. In the context of the free peptide, these additional residues are believed to confer increased affinity for the GLP-1 receptor and greater protease resistance. However, it may also be responsible to some degree for the immunogenicity of the peptide. Two further constructs were made, using substantially the same procedure as described above, to make constructs with only the sequence homologous to GLP-1, i.e., exendin-4(1-31) or exendin-4(1-30), by deletion of the DNA sequence coding for residues 32-39 or 31-39, respectively. For exendin-4(1-31), primers P0904 (SEQ ID NO: 35) and P0941 (SEQ ID NO: 36) were used and the appropriate products were ligated (pREX0629/pREX0658). For exendin-4(1-30), primers P0942 (SEQ ID NO: 37) and P0943 (SEQ ID NO: 38) were used and the appropriate products were ligated (pREX0630/pREX0659).

Constructs were also made with the exendin-4 (1-39) sequence and alternative linkers, e.g., (GGGGS)$_3$ (SEQ ID NO: 39), PEAPTD (pREX1005) (SEQ ID NO: 6), or an IgG hinge (pREX0938) (SEQ ID NOs: 7-16).

Additional Exendin-4/Tf Constructs with Other Signal Sequences—Impact on Relative Productivity Constructs were created to express exendin-4/mTf (SEQ ID NO: 23; encoded by SEQ ID NO: 24) linked to the signal sequences HSA/MFα-1 (pREX 1354) (SEQ ID NO: 40; encoded by SEQ ID NO: 41) and modified HSA/MFα-1 (pREX 1345) (SEQ ID NO: 42; encoded by SEQ ID NO: 43). A comparison of productivity of yeast strains expressing the exendin-4/mTf with the three different signal sequences revealed a relative productivity ratio as follows for transferrin signal sequence (nL)/HSA/MFα-1/Modified HSA/MFα-1: 1/1.75/1.32.

Example 2

Determination of Potency of Exendin-4/Tf Fusion Proteins

Potency was calculated from the measured response of cAMP produced as a result of GLP-1 receptor-mediated ligand binding in CHO cells transfected with the rat GLP-1 receptor (CHO-GLP-1R) following incubation with samples. 96-well tissue culture plates were seeded with CHO-GLP-1R cells and cultured overnight. The following day, the cells were rinsed with Krebs-Ringer buffer (KRB) and incubated in KRB containing the phosphodiesterase inhibitor 3-isobutyl-1-methylxanthine (IBMX, 2 mM) to inhibit intracellular enzymes that process cAMP. Serial dilutions of test compounds and controls were prepared in KRB/IBMX and triplicate wells of cells were inoculated with samples and controls. After incubation, individual sample lysates were then assayed to measure the increase in intracellular cAMP levels using a competition-based fluorescent immunoassay (Catch-Point® cAMP Fluorescent Assay Kit, Molecular Devices Corp., Sunnyvale, Calif.). The amount of cAMP accumulation in cells after GLP-1 receptor-mediated ligand binding is used to determine bioactivity and relative potency.

The data in Table 1 indicate that the exendin-4/Tf fusions are more potent in activating the GLP-1 receptor than the GLP-1(7-37,A8G,K34A) (PEAPTD)$_2$ (SEQ ID NO: 5) mTf fusion protein. The mTf moiety in each fusion protein had the amino acid sequence as shown in SEQ ID NO: 17.

TABLE 1

Potency of GLP-1/mTf and Exendin-4/Tf fusion proteins

| Plasmid | Construct | | | Potency (nM) |
|---|---|---|---|---|
| pREX0585 | GLP-1(7-37; A8G, K34A) | (PEAPTD)$_2$ | mTf | 1.3 |
| pREX0659 | Exendin-4(1-30) | (PEAPTD)$_2$ | mTf | 0.85 |
| pREX0658 | Exendin-4(1-31) | (PEAPTD)$_2$ | mTf | 0.33 |
| pREX0936 | Exendin-4(1-39) | (PEAPTD)$_2$ | mTf | 0.16 |

Example 3

Figure 1A:
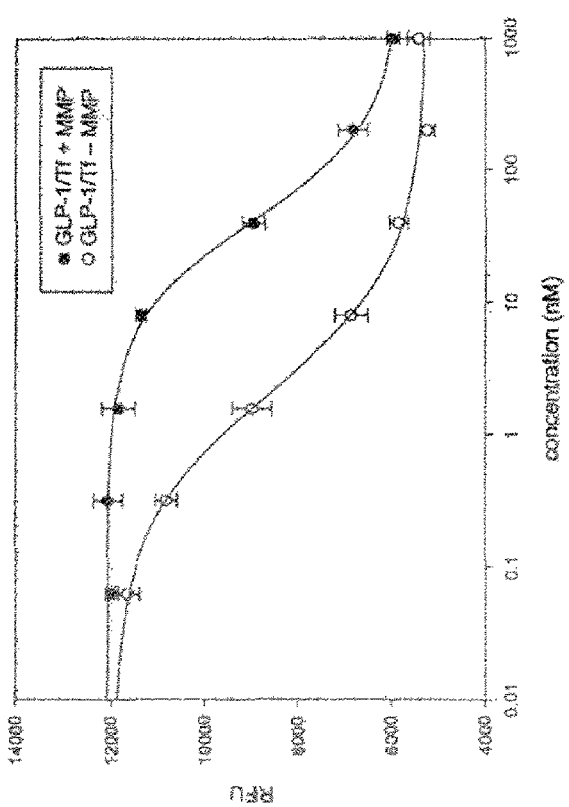
FIG. 1A is a graph showing collagenase resistance (MMP is matrix metalloprotease 1) in vitro for the GLP-1(7-37, A8G,K34A) (PEAPTD)$_2$ (SEQ ID NO: 5) mTf fusion protein (GLP-1/Tf).

MMP-Resistance of the Exendin-4(1-39) (PEAPTD)$_2$ (SEQ ID NO: 5) mTf Fusion Protein The exendin-4(1-39) (PEAPTD)$_2$ (SEQ ID NO: 5) mTf fusion protein (SEQ ID NO: 23) was tested for resistance to inactivation by matrix metalloprotease I (MMP-1, collagenase) in vitro. Samples of exendin-4(1-39) (PEAPTD)$_2$ (SEQ ID NO: 5) mTf fusion protein and the GLP-1(7-37,A8G, K34A) (PEAPTD)$_2$ (SEQ ID NO: 5) mTf fusion protein were incubated with recombinant MMP-1 for 48 hr at 37° C. and then tested for activity. When comparing FIG. 1A with FIG. 1B, it can be seen that the exendin-4/Tf fusion protein is resistant to inactivation by MMP-1 (FIG. 1B), in contrast to the GLP-1/mTf fusion protein (FIG. 1A). This difference in degradation occurs despite the close similarity in amino acid sequence in the active portion of the molecules.

Example 4

Figure 2:
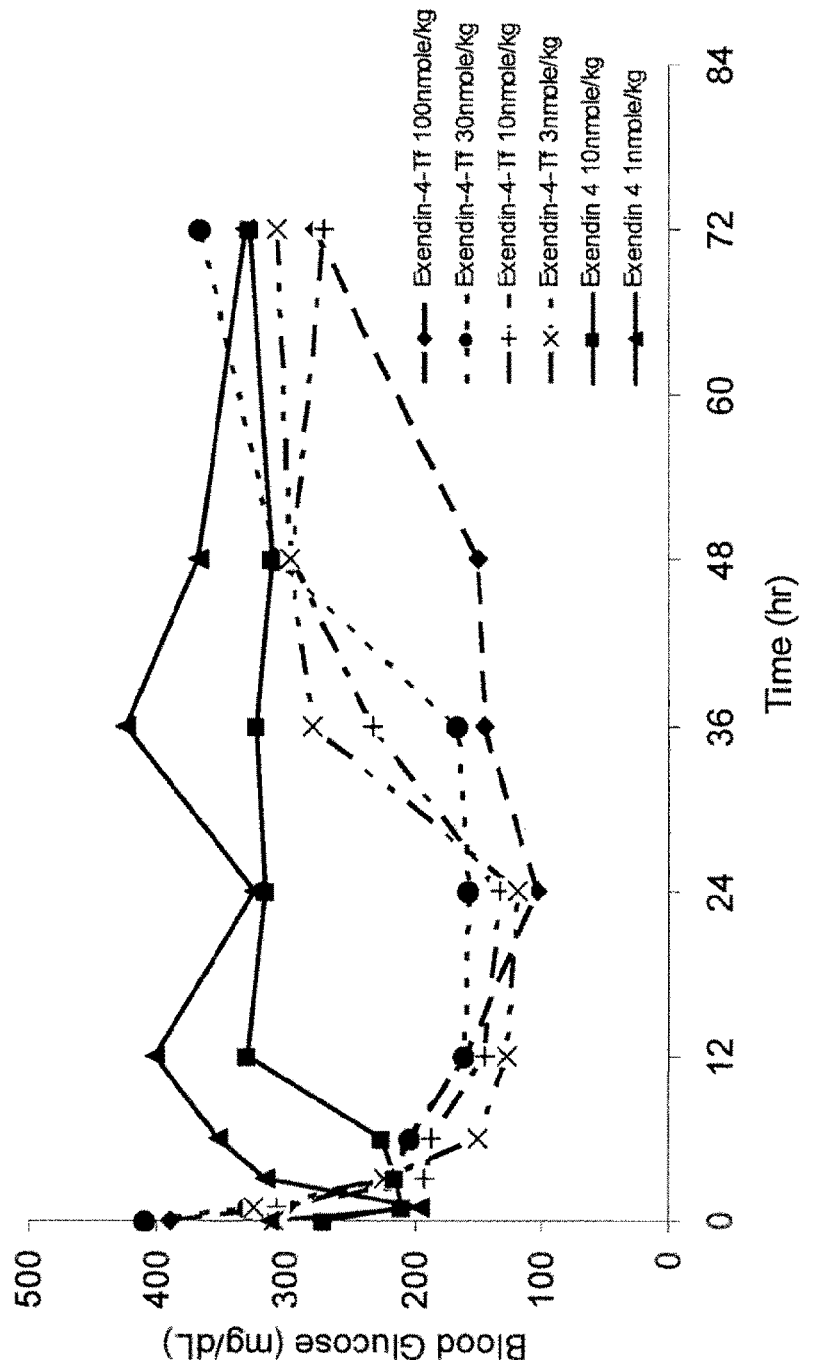
FIG. 2 is a graph showing the dose effect of the exendin-4 (1-39) (PEAPTD)$_2$ (SEQ ID NO: 5) mTf fusion protein (Exendin-4/Tf) on blood glucose in diabetic (db/db) mice, and shows a comparative effect for the exendin-4 control. Each point represents the average glucose measurement (n=3).

Effect of the Exendin-4(1-39) (PEAPTD)$_2$ (SEQ ID NO: 5) mTf Fusion Protein on Blood Glucose in Diabetic Mice Diabetic (db/db) mice were injected with various doses of the exendin-4(1-39) (PEAPTD)$_2$ (SEQ ID NO: 5) mTf fusion protein (SEQ ID NO: 23), the GLP-1(7-37,A8G,K34A) (PEAPTD)$_2$ mTf fusion protein, or exendin-4 peptide (Bachem, King of Prussia, Pa.) and blood glucose concentrations were monitored by analyzing blood samples using a glucometer. As shown in FIG. 2, doses of the exendin-4(1-39) (PEAPTD)$_2$ (SEQ ID NO: 5) mTf fusion protein as low as 1.3 nmole/kg significantly reduced the blood glucose in these animals by 3 hours after subcutaneous injection. The glucose level almost normalized in all treatment groups and this level persisted for 24 hours. The glucose concentrations gradually increased to the pretreatment levels between 48-72 hours post-treatment, depending on the dose administered. Exendin-4 peptide did not lower blood glucose as much as the exendin-4(1-39) (PEAPTD)$_2$ (SEQ ID NO: 5) mTf fusion protein, regardless of the dose, and the exendin-4 glucose lowering effect had completely dissipated by about 12 hours. This is consistent with literature reports that the maximum reduction in blood glucose achievable with exendin-4 is approximately 37%; the reduction seen with the exendin-4(1-39) (PEAPTD)$_2$ (SEQ ID NO: 5) mTf fusion protein was approximately 70%. The effect of the exendin-4(1-39) (PEAPTD)$_2$ (SEQ ID NO: 5) mTf fusion protein on blood glucose was also significantly greater and of a longer duration than equivalent doses of the GLP-1(7-37,A8G,K34A) (PEAPTD)$_2$ (SEQ ID NO: 5) mTf fusion protein.

Example 5

Effect of the Exendin-4(1-39) (PEAPTD)$_2$ (SEQ ID NO: 5) mTf Fusion Protein on Rat Body Weight Sprague Dawley rats were injected subcutaneously with different doses of the exendin-4(1-39) (PEAPTD)$_2$ (SEQ ID NO: 5) mTf fusion protein (SEQ ID NO: 23), and the exendin-4 peptide. mTf or saline was used as control. The rats were weighed everyday (prior to dosing on dosing days). Animals had full access to food and water at all times.

Figure 3:
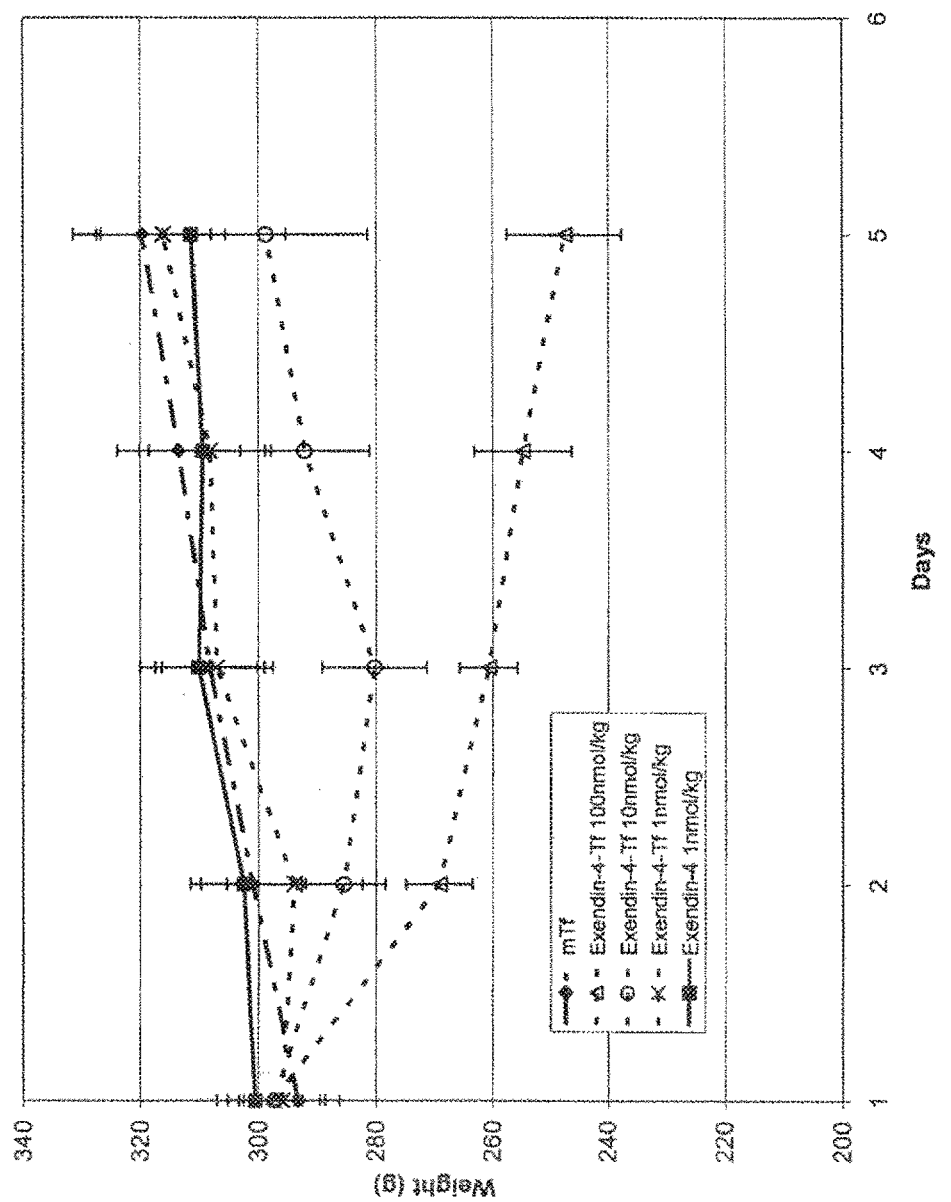
FIG. 3 is a graph showing the dose effect of daily injections of the exendin-4(1-39) (PEAPTD)$_2$ (SEQ ID NO: 5) mTf fusion protein (Exendin-4/Tf) on body weight, and shows a comparative effect for exendin-4 and for the mTf controls.

As shown in FIG. 3, the animals treated with 10 and 100 nmole/kg doses of the exendin-4(1-39) (PEAPTD)$_2$ (SEQ ID NO: 5) mTf fusion protein lost weight after the first injection and the weight loss continued for the entire administration period. By day five, the animals treated with 100 nmole/kg doses lost an average of 75 grams (17%) body weight compared to controls, and the weight loss is related to a drop in food and water intake. Because of the dramatic and acute weight loss observed, daily administration of the drug was stopped at day five. After the 5 day administration period, all animals gained weight at a similar rate. However, the exendin-4(1-39) (PEAPTD)$_2$ (SEQ ID NO: 5) mTf fusion protein treated groups, especially the high dose group, still weighed less than the control animals at 20 days following the last administration.

Example 6

Figure 4:
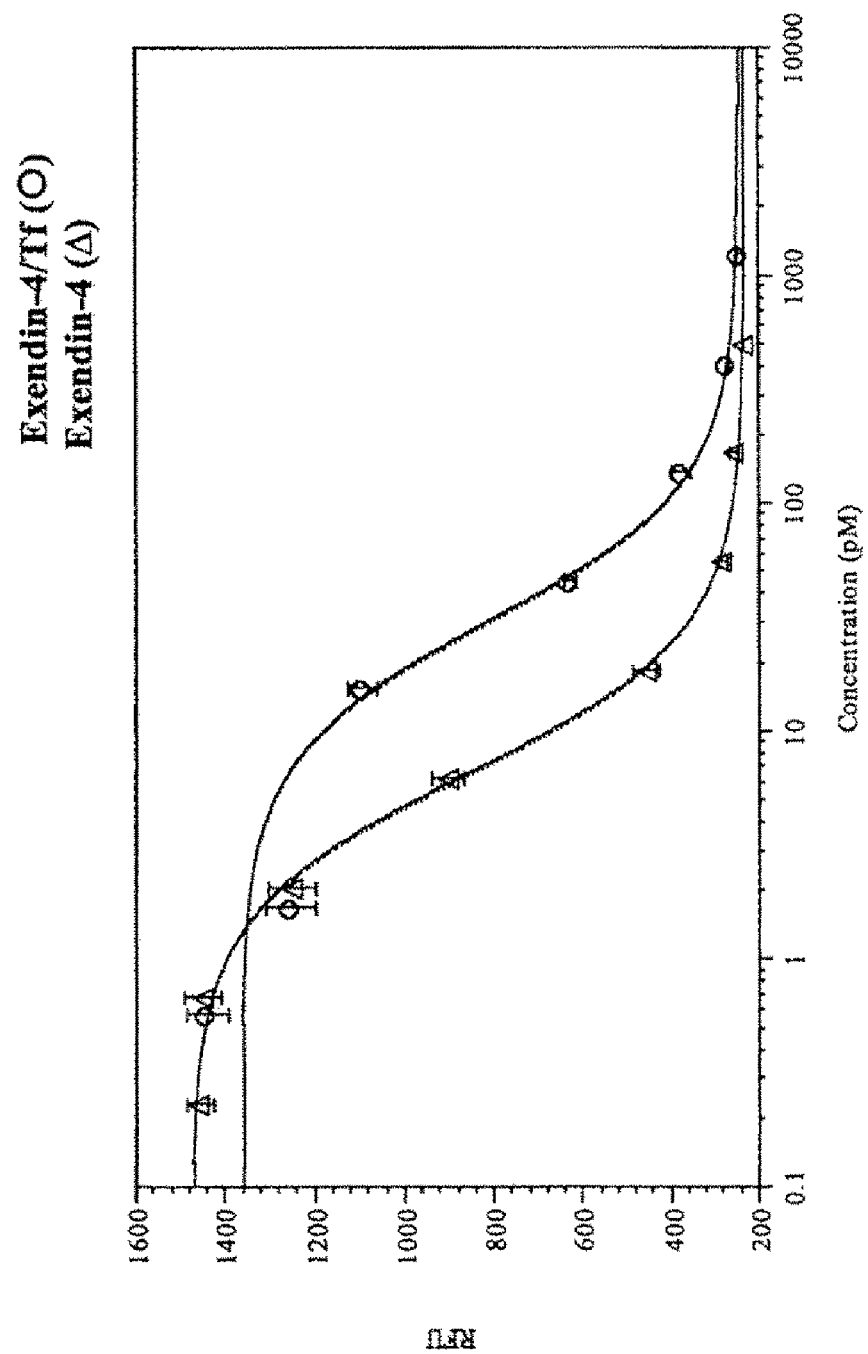
FIG. 4 is a graph comparing the relative potency for the exendin-4(1-39) (PEAPTD)$_2$ (SEQ ID NO: 5) mTf fusion protein (Exendin-4/Tf) and exendin-4. This was determined by a cell-based cAMP assay. The EC50 for the exendin-4(1-39) (PEAPTD)$_2$ (SEQ ID NO: 5) mTf fusion protein is 31.3 pM and the EC50 for exendin-4 is 6.6 pM.

Predictive Dose for Exendin-4(1-39) (PEAPTD)$_2$ (SEQ ID NO: 5) mTf Fusion Protein for Glycemic Control in Type II Diabetics and for Weight Loss Based on published data, a therapeutic single dose of 10 μg of exenatide (BYETTA®) produced a Cmax of 200 pg/mL in humans. The molecular size difference between exenatide and the exendin-4(1-39) (PEAPTD)$_2$ (SEQ ID NO: 5) mTf fusion protein (SEQ ID NO: 23) (4.2 kDa vs. 80.5 kDa) indicates that an exendin-4(1-39) (PEAPTD)$_2$ (SEQ ID NO: 5) mTf fusion protein blood level of approximately 3.8 ng/mL to be equivalent to the therapeutic level of exenatide in terms of blood glucose lowering effect. In addition to the size, the exendin-4(1-39) (PEAPTD)$_2$ (SEQ ID NO: 5) mTf fusion protein is approximately 5-fold less potent than exendin-4 based on in vitro testing in CHO cells expressing the human GLP-1 receptor (FIG. 4). Therefore, to achieve the similar therapeutic activity of 10 μg of exenatide, a circulating concentration of approximately 20 ng/mL of exendin-4(1-39) (PEAPTD)$_2$ (SEQ ID NO: 5) mTf fusion protein would be required.

The exendin-4(1-39) (PEAPTD)$_2$ (SEQ ID NO: 5) mTf fusion protein and the GLP-1(7-37,A8G,K34A) (PEAPTD)$_2$ (SEQ ID NO: 5) mTf fusion protein are similar both in size and structure. The molecular weight for the exendin-4(1-39) (PEAPTD)$_2$ (SEQ ID NO: 5) mTf fusion protein is 80.5 kDa and for the GLP-1(7-37,A8G,K34A) (PEAPTD)$_2$ (SEQ ID NO: 5) mTf fusion protein is 79.6 kDa. The exendin-4(1-39) (PEAPTD)$_2$ (SEQ ID NO: 5) mTf fusion protein is approximately four-eight fold more potent than the GLP-1(7-37,A8G,K34A) (PEAPTD)$_2$ (SEQ ID NO: 5) mTf fusion protein. Mean pharmacokinetic parameters of the exendin-4(1-39) (PEAPTD)$_2$ (SEQ ID NO: 5) mTf fusion protein following intravenous and subcutaneous administration of 1 mg/kg to Cynomolgus monkey are presented in the Table 2. Mean pharmacokinetic parameters of the GLP-1(7-37,A8G,K34A) (PEAPTD)$_2$ (SEQ ID NO: 5) mTf fusion protein following subcutaneous administration of 0.6 mg/kg to Cynomolgus monkey are presented in the Table 3.

TABLE 2

Summary of mean pharmacokinetic parameters for the exendin-4(1-39) (PEAPTD)$_2$ (SEQ ID NO: 5) mTf fusion protein after intravenous and subcutaneous administration of 1 mg/kg to male and female Cynomolgus monkeys

| Parameter | Intravenous | Subcutaneous |
|---|---|---|
| Cmax (ng/mL) | 33,981 ± 14,826 (4) | 5,236 ± 1,038 (4) |
| Tmax (h) | 0.542 (4) | 9.02 (4) |
| AUC(0-t) (h · ng/mL) | 567,364 ± 68,102 (4) | 278,067 ± 24,367 (4) |
| AUC(inf) (h · ng/mL) | 572,314 ± 68,660 (4) | 280,279 ± 29,261 (3) |
| λ z (h − 1) | 0.0313 ± 0.0137 (4) | 0.0252 ± 0.0084 (3) |
| t½ (h) | 25.5 ± 10.3 (4) | 29.3 ± 08.2 (3) |
| CL (mL/min/kg) | 1.77 ± 0.24 (4) | — |
| Vz (mL/kg) | 65.9 ± 31.0 (4) | — |
| F (%) | — | 49.0 |

TABLE 3

Summary of mean pharmacokinetic parameters for the GLP-1(7-37, A8G, K34A) (PEAPTD)$_2$ (SEQ ID NO: 5) mTf fusion protein after subcutaneous administration of 0.6 mg/kg to male and female Cynomolgus monkeys

| Parameter | Males | Females |
|---|---|---|
| Cmax (ng/mL) | 2,922 ± 1,530 (3) | 3,173 ± 1,767 (3) |
| Tmax (h) | 12.0 (3) | 24.2 (3) |
| AUC(0-t) (h · ng/mL) | 168,087 ± 58,749 (3) | 165,474 ± 32,756 (3) |
| AUC(inf) (h · ng/mL) | 171,963 ± 61,998 (3) | 186,065 ± 140 (2) |
| λ z (h − 1) | 0.0216 ± 0.0042 (3) | 0.0250 ± 0.0002 (2) |
| t½ (h) | 32.9 ± 6.78 (3) | 27.7 ± 0.23 (2) |
| CL (mL/min/kg) | — | — |
| Vz (mL/kg) | — | — |
| F (%) | — | — |

In a separate experiment, the bioavailability of the GLP-1(7-37, A8G, K34A) (PEAPTD)$_2$ (SEQ ID NO: 5) mTf fusion protein was shown to be approximately 50% in Cynomolgus monkeys.

The elimination half-life ($t_{1/2}$) of exendin-4(1-39) (PEAPTD)$_2$ (SEQ ID NO: 5) mTf fusion protein for both intravenous and subcutaneous administration, range of Tmax, and the bioavailability (F(%)) were similar to the GLP-1(7-37,A8G,K34A) (PEAPTD)$_2$ (SEQ ID NO: 5) mTf fusion protein's monkey pharmacokinetic parameters.

Previous human experience with the GLP-1(7-37,A8G,K34A) (PEAPTD)$_2$ (SEQ ID NO: 5) mTf fusion protein indicated that the pharmacokinetics was linear from doses 30 μg/kg to 900 μg/kg, with mean Tmax at 48 hours, and mean $t_{1/2}$ was about 50 hours. The Cmax was 758±435 ng/mL at a dose of 300 μg/kg (or 30 mg/100 kg patient) and 1,609±805 ng/mL at a dose of 900 μg/kg (90 mg/100 kg patient). However, the fusion protein did not show a robust effect on blood glucose levels in diabetic subjects at these doses, nor at a dose of 1800 μg/kg.

Due to the similarity in size and structure, as well as the similar preclinical pharmacokinetic profile in monkeys between these two compounds, the pharmacokinetic characteristics of the exendin-4(1-39) (PEAPTD)$_2$ (SEQ ID NO: 5) mTf fusion protein in humans are predicted to be similar to the GLP-1(7-37,A8G,K34A) (PEAPTD)$_2$ (SEQ ID NO: 5) mTf fusion protein.

Based upon similarities to GLP-1(7-37,A8G,K34A) (PEAPTD)$_2$ (SEQ ID NO: 5) mTf, a relative four-eight fold higher in vitro potency of exendin-4(1-39) (PEAPTD)$_2$ (SEQ ID NO: 5) mTf fusion protein compared to GLP-1(7-37,A8G,K34A) (PEAPTD)$_2$ (SEQ ID NO: 5) mTf, and the relative five-fold decrease in in vitro potency for exendin-4(1-39) (PEAPTD)$_2$ (SEQ ID NO: 5) mTf fusion protein as compared to exenatide, it is surprising that an exendin-4(1-39) (PEAPTD)$_2$ (SEQ ID NO: 5) mTf fusion protein dose of 2 mg can have a glucose lowering effect. Further, a dose of 10 mg per subject, on a weekly dosing basis, would be needed to achieve a steady-state Cmin of 20 ng/mL. Thus, the efficacious dose of the exendin-4(1-39) (PEAPTD)$_2$ (SEQ ID NO: 5) mTf fusion protein (SEQ ID NO: 23) for therapeutic blood glucose lowering ranges from 0.5 to 50 mg per dose administered on a weekly dose basis. Such a dose can also be administered once per two weeks or once per month.

In addition to its effect on blood glucose, the exendin-4(1-39) (PEAPTD)$_2$ (SEQ ID NO: 5) mTf fusion protein at or above 10 nmole/kg was correlated with a reduction in animal body weight in mice and rats. Twenty-four hours after administration of a single dose of 10 or 100 nmole/kg of the exendin-4(1-39) (PEAPTD)$_2$ (SEQ ID NO: 5) mTf fusion protein to mice that resulted in an average drop in body weight of 6% and 14%, respectively compared to a mean loss of 1% in the control or 1 nmole/kg exendin-4 treated animals. Daily administration of exendin-4(1-39) (PEAPTD)$_2$ (SEQ ID NO: 5) mTf fusion protein also resulted in 16% weight loss in rats at dose of 100 nmole/kg. Weight loss can be attributed to reduced food intake observed in animals dosed with the exendin-4(1-39) (PEAPTD)$_2$ (SEQ ID NO: 5) mTf fusion protein, which is a known pharmacologic effect of GLP-1 receptor activation. Available data indicate that the required dose for weight loss is about 2-3 fold higher than the doses needed for glucose lowering. Thus, the efficacious dose of the exendin-4(1-39) (PEAPTD)$_2$ (SEQ ID NO: 5) mTf fusion protein (SEQ ID NO: 23) for weight toss ranges from 1.0 to 100 mg per dose, administered once per week. Such a dose can also be administered once per two weeks or once per month.

Example 7

Delivery of the Exendin-4(1-39) (PEAPTD)$_2$ (SEQ ID NO: 5) mTf Fusion Protein by Inhalation Aerosols were generated with an Aerotech II compressed air jet nebulizer (CIS-US Inc., Bedford, Mass.) and directed through a 1.58 cm diameter stainless steel aerosol delivery line into a 24-port flow past rodent exposure system (IN-TOX, ABQ, NM). The exhaust flow rate out of the chamber was ~11.5 L/min. The nebulizer pressure was maintained at ~30 psi.

To test the effect of aerosolization on the fusion protein, a 10 mg/mL solution of the exendin-4(1-39) (PEAPTD)$_2$ (SEQ ID NO: 5) mTf fusion protein (SEQ ID NO:23) in 10 mM histidine pH 7.4, 100 mM NaCl was nebulized and 5 mL of condensed liquid from the aerosol was subsequently collected in a biosampler over an eight minute period and tested for its integrity and activity. The aerosolization procedure had no detectable adverse effect on the structure of the exendin-4(1-39) (PEAPTD)$_2$ (SEQ ID NO: 5) mTf fusion protein as judged by SDS-PAGE and SEC-HPLC; there was no apparent breakdown or aggregate formation. The recovered material was also shown to be biologically active.

For the in vivo test, diabetic mice (db/db) were positioned in the inhalation chambers and allowed to breathe an aerosolized exendin-4(1-39) (PEAPTD)$_2$ (SEQ ID NO: 5) mTf fusion protein for various lengths of time. At the end of the inhalation exposure period mice were then monitored for blood glucose for the next 72 hours. The inhalation time in the chamber was chosen so that the animals would receive an exposure equivalent to the 0.3, 1 and 3 mg/kg dose administered subcutaneously. As a control, these doses were administered subcutaneously (SC) to compare in vivo activity to the inhaled route of administration. Blood glucose levels in the animals receiving the exendin-4(1-39) (PEAPTD)$_2$ (SEQ ID NO: 5) mTf fusion protein by inhalation showed a significant drop following exposure to the drug. Evaluation of the circulating levels of the exendin-4(1-39) (PEAPTD)$_2$ (SEQ ID NO: 5) mTf fusion protein indicated a bioavailability of approximately 10% for this non-optimized system and formulation.

The invention claimed is:

1. A fusion protein comprising an exendin-4 fused to a modified transferrin (mTf), wherein said fusion protein comprises the amino acid sequence as shown in SEQ ID NO: 23.

2. A pharmaceutical composition comprising the fusion protein of claim 1 and a pharmaceutically acceptable carrier.

3. The pharmaceutical composition of claim 2, wherein the composition is adapted to be administered at a dose ranging from 0.5 mg to 50 mg.

4. The pharmaceutical composition of claim 2, wherein the composition is adapted to be administered at a dose of 1 mg to 100 mg.

5. The pharmaceutical composition of claim 2, wherein the composition is adapted to be administered via inhalation.

* * * * *